(12) United States Patent
Chen et al.

(10) Patent No.: US 10,582,907 B2
(45) Date of Patent: Mar. 10, 2020

(54) DEEP LEARNING BASED BONE REMOVAL IN COMPUTED TOMOGRAPHY ANGIOGRAPHY

(71) Applicant: Siemens Healthcare GmbH, Erlangen (DE)

(72) Inventors: Mingqing Chen, Plainsboro, NJ (US); Tae Soo Kim, Baltimore, MD (US); Jan Kretschmer, Nürnberg (DE); Sebastian Seifert, Erlangen (DE); Shaohua Kevin Zhou, Plainsboro, NJ (US); Max Schöbinger, Hirschaid (DE); David Liu, Plano, TX (US); Zhoubing Xu, Plainsboro, NJ (US); Sasa Grbic, Plainsboro, NJ (US); He Zhang, Edison, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 208 days.

(21) Appl. No.: 15/727,677

(22) Filed: Oct. 9, 2017

(65) Prior Publication Data
US 2018/0116620 A1  May 3, 2018

Related U.S. Application Data

(60) Provisional application No. 62/415,075, filed on Oct. 31, 2016.

(51) Int. Cl.
*A61B 6/00* (2006.01)
*G06T 7/136* (2017.01)
(Continued)

(52) U.S. Cl.
CPC .............. *A61B 6/5252* (2013.01); *A61B 6/03* (2013.01); *A61B 6/504* (2013.01); *G06K 9/34* (2013.01);
(Continued)

(58) Field of Classification Search
CPC ......... A61B 6/5252; A61B 6/03; A61B 6/504; G06K 9/34; G06T 7/136; G06T 7/11; G06T 2200/04
See application file for complete search history.

(56) References Cited

U.S. PATENT DOCUMENTS 8,244,015 B2 * 8/2012 Sirohey .................. A61B 6/504
 382/130
9,710,880 B2 * 7/2017 Xu ........................ G06T 11/003
(Continued)

OTHER PUBLICATIONS

Extended European Search Report dated Mar. 2, 2018 in corresponding European application No. 17198839.7.
(Continued)

*Primary Examiner* — Anand P Bhatnagar

(57) ABSTRACT

A method and apparatus for deep learning based automatic bone removal in medical images, such as computed tomography angiography (CTA) volumes, is disclosed. Bone structures are segmented in a 3D medical image of a patient by classifying voxels of the 3D medical image as bone or non-bone voxels using a deep neural network trained for bone segmentation. A 3D visualization of non-bone structures in the 3D medical image is generated by removing voxels classified as bone voxels from a 3D visualization of the 3D medical image.

18 Claims, 18 Drawing Sheets

(51) Int. Cl.
*G06T 7/11* (2017.01)
*A61B 6/03* (2006.01)
*G06K 9/34* (2006.01)

(52) U.S. Cl.
CPC ............... *G06T 7/11* (2017.01); *G06T 7/136* (2017.01); *G06T 2200/04* (2013.01); *G06T 2207/10081* (2013.01); *G06T 2207/20036* (2013.01); *G06T 2207/20081* (2013.01); *G06T 2207/30008* (2013.01); *G06T 2207/30101* (2013.01)

(56) References Cited

U.S. PATENT DOCUMENTS

| | | | |
|---|---|---|---|
| 9,760,807 | B2 | 9/2017 | Zhou et al. |
| 9,984,460 | B2 * | 5/2018 | Westerhoff ............ G06T 7/0012 |
| 10,062,014 | B2 | 8/2018 | Zhou et al. |
| 10,134,141 | B2 * | 11/2018 | Xu ........................ G06N 3/0454 |
| 10,346,981 | B2 * | 7/2019 | Anderson ............... G16H 50/30 |
| 2009/0003677 | A1 * | 1/2009 | Wang .................... G06F 19/321 382/131 |
| 2009/0161939 | A1 | 6/2009 | Wu et al. |
| 2016/0210749 | A1 | 7/2016 | Nguyen et al. |
| 2016/0328855 | A1 * | 11/2016 | Lay .......................... G06T 5/005 |
| 2018/0330207 | A1 | 11/2018 | Zhou et al. |

OTHER PUBLICATIONS

Milletari Fausto et al: "Robust Segmentation of Various Anatomies in 30 Ultrasound Using Hough Forests and Learned Data Representations", Nov. 20, 2015, ECCV 2016 Conference; [Lecture Notes in Computer Science; Lect.Notes Computer], Springer International Publishing, CHAM, pp. 111-118.

Cosmin Cernazanu-Glavan et al: "Segmentation of bone structure in X-ray images using convolutional neural network", Advances in Electrical and Computer Engineering, Jan. 1, 2013; Retrieved from the Internet: URL:http://staff.cs.upt.ro/-cosminc/papers/aece2013.pdf.

Max Jaderberg et al: "Speeding up Convolutional Neural Networks with Low Rank Expansions", Proceedings of the British Machine Vision Conference 2014, May 15, 2014; pp. 1-12.

Tomandl BF, Hammen T, Klotz E, Ditt H, Stemper B, Lell M. Bone-subtraction CT angiography for the evaluation of intracranial aneurysms. AJNR Am J Neuroradiol. Jan. 2006;27(1):55-9. www.healthcare.siemens.com/computed-tomography/options-upgrades/clinical-applications/syngo-ct-vascular-analysis/features; retrieved on the Internet; 2017.

Horst K. Hahn, Markus T. Wenzel, Johann Drexl, Susanne Zentis, Heinz-Otto Peitgen, HWT—hybrid watershed transform: optimal combination of hierarchical interactive and automated image segmentation. Proc. SPIE 6512, Medical Imaging 2007: Image Processing, 65120Z (Mar. 3, 2007).

Johnson PT, Hahn HK, Heath DG, Fishman EK. Automated Multidetector Row CT Dataset Segmentation with an Interactive Watershed Transform (IWT) Algorithm: Part 2—Body CT Angiographic and Orthopedic Applications. Journal of Digital Imaging. 2008;21(4):413-421.

Quan Wang, Dijia Wu, Le Lu, Meizhu Liu, Kim L. Boyer, Shaohua Kevin Zhou, Semantic Context Forests for Learning-Based Knee Cartilage Segmentation in 3D MR Images. Medical Computer Vision. Large Data in medical Imaging: 3rd International MICCAI Workshop, MCV 2013, 105-115.

Zhuowen Tu, "Probabilistic boosting-tree: learning discriminative models for classification, recognition, and clustering," Tenth IEEE International Conference on Computer Vision (ICCV'05) vol. 1, Beijing, 2005, pp. 1589-1596 vol. 2.

Alex Krizhevsky, Ilya Sutskever, Geoffrey E. Hinton, Imagenet classification with deep convolutional neural networks. Advances in Neural Information Processing Systems, 2012, 1106-1114.

K. Simonyan, A. Zisserman. Very deep convolutional networks for large-scale image classification. ICLR, 2015.

Kaiming He, Xiangyu Zhang, Shaoqing Ren, Jian Sun. Deep Residual Learning for Image Recognition. CoRR, 2015.

Pavel Karas, David Svoboba. Convolution of large 3D images on GPU and its decomposition. EURASIP Journal on Advances in Signal Processing, 2011, pp. 120.

Alvarez, J., Peterson, L. DecomposeMe: Simplifying ConvNets for end-to-end learning. CoRR 2016.

Yani Ioannou, Duncan P. Roertson, Antonio Criminisi. Deep Roots: Improving CNN Efficiency with Hierarchical Filter Groups. CoRR, 2016.

Vijay Badrinarayanan, Alex Kendall, Roberto CipollaSegNet: A Deep Convolutional Encoder-Decoder Architecture for Image Segmentation, CoRR, 2015.

Zhao, Hengshuang, et al. "Pyramid Scene Parsing Network." arXiv preprint arXiv:1612.01105 (2016).

* cited by examiner

DEEP LEARNING BASED BONE REMOVAL IN COMPUTED TOMOGRAPHY ANGIOGRAPHY

This application claims the benefit of U.S. Provisional Application No. 62/415,075, filed Oct. 31, 2016, the disclosure of which is herein incorporated by reference.

BACKGROUND OF THE INVENTION

The present invention relates to bone segmentation and removal in medical image data, and more particularly, to automated removal of bone voxels from 3D computed tomography angiography images in order to visualize vessels in the 3D computed tomography angiography images.

Bone segmentation and removal in computed tomography angiography (CTA) is an important clinical application. CTA is a medical imaging technique that is often used to visualize the blood vessels in a patient's body. Computed tomography (CT) combines a series of X-ray images taken from different angles and uses computer processing to create cross-sectional images, or slices, of bones, blood vessels and soft tissues inside the body. The cross-sectional images, or slices, can be combined to generate 3D CT volumes. In CTA, a contrast agent is injected into the bloodstream of the patient prior to CT imaging in order to generate contrast enhanced CT images that visualize the patient's vessels. CTA volumes can be visualized using a volume rendering technique (VRT) so that clinicians are able to see 3D vascular structures and pathologies such as stenoses and aneurysms. The goal of bone removal is to segment and remove bone voxels from CTA volumes to yield a vascular-only view, which provides an unhindered 3D view of the vascular structures in the CTA volume.

In CTA images, there is an overlapping intensity between the distributions of bones and contrast enhanced vessels. That is bone and contrast enhance vessels appear with similar intensity in CTA images. Accordingly, bones can be a major obstacle in the visualization and analysis of vessel trees, aneurisms, and calcifications using CTA, and it is desirable to remove bone structures from CTA images in order to achieve a better visualization of the vessels. In the past, manual editing techniques have been used to extract and remove bone structures from the image data. However, the tedious and long operating time required for manual editing is prohibitive for it to be of practical use. Furthermore, due to image resolution and noise in the image data, bones and vessels with overlapping intensity distributions often appear to be connected, which creates significant challenges in automated segmentation and removal of bone structures from the image data.

Automatic bone removal in CTA volumes is a challenging task, due to the fact that many osseous and vascular structures have similar patterns in shape and contrast. Previous approaches generally can be categorized into top-down and bottom-up approaches. Top-down approaches include statistical shape model and image atlas based approaches. These approaches typically need strong initial information about the body region or landmark location, which make them difficult to apply in various field of views (FOV). In the bottom-up category, many approaches are designed for non-contrasted scans, including region-growing and super-voxel approaches. However, in CTA volumes, the existence of contrast agent enhances vessel intensities and significantly increases the complexity of the problem, and such approaches have difficulty is differentiating bone and non-bone regions in some regions in CTA volumes (e.g., subclavian) due to weak gradient and highly similar appearance of the bone and non-bone regions.

BRIEF SUMMARY OF THE INVENTION

The present invention provides a method and system for deep learning based bone removal in computed tomography angiography (CTA) images.

In an embodiment of the present invention, bone structures are segmented in a 3D medical image of a patient by classifying voxels of the 3D medical image as bone or non-bone voxels using a deep neural network trained for bone segmentation. A 3D visualization of non-bone structures in the 3D medical image is generated by removing voxels classified as bone voxels from a 3D visualization of the 3D medical image.

These and other advantages of the invention will be apparent to those of ordinary skill in the art by reference to the following detailed description and the accompanying drawings.

DETAILED DESCRIPTION

The present invention relates to a method and system for deep learning based bone removal in computed tomography angiography (CTA) images. Embodiments of the present invention are described herein to give a visual understanding of the deep learning based bone removal method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
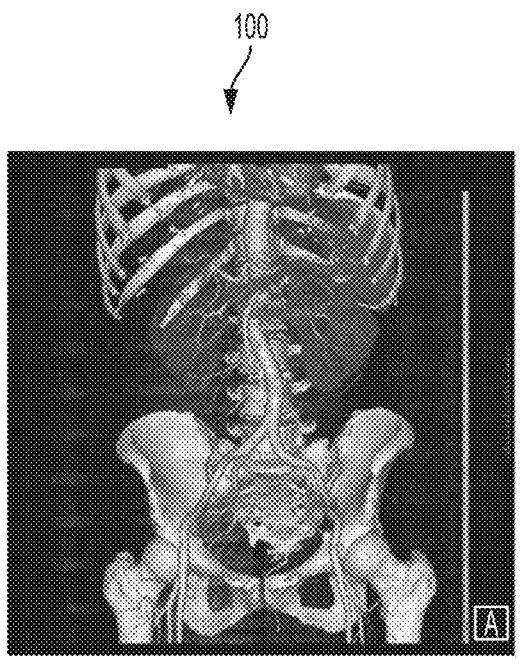
FIG. 1 illustrates exemplary bone segmentation results of a computed tomography angiography (CTA) volume using various techniques.
Figure 1:
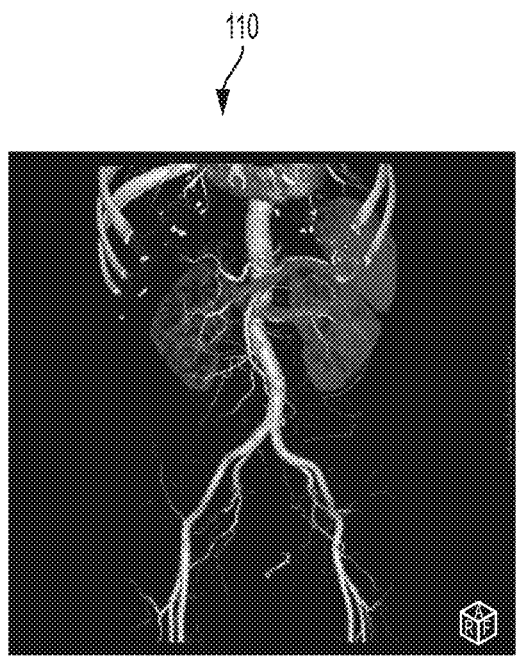
Figure 1:
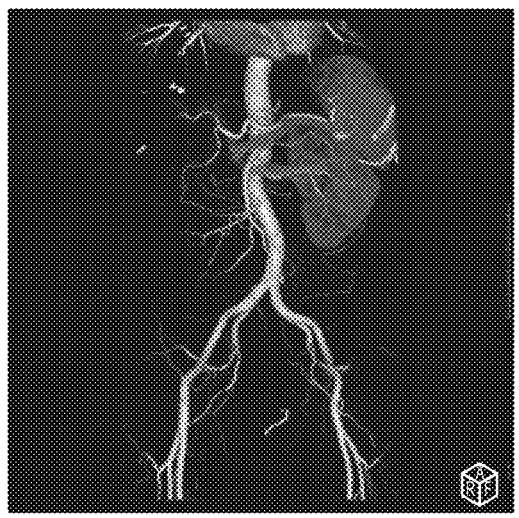
Figure 1:
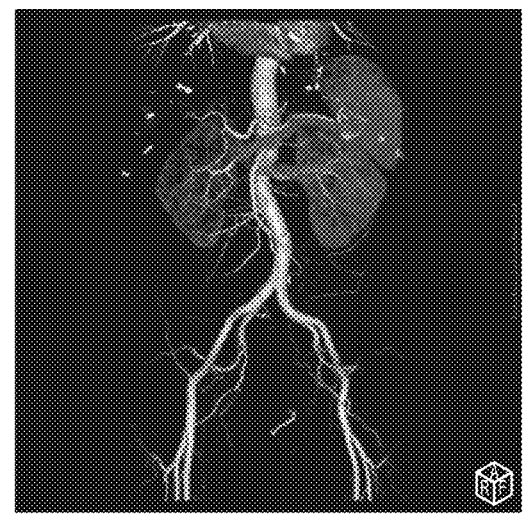

Automatic removal on bones in CTA images is a challenging task, due to the fact that many osseous and vascular structures have similar patterns of shape and contrast. The close proximity of bones and vessels, such as the vessels close to the skull base or the part of the aorta close to the spine, further complicates automated bone segmentation and removal. One existing technique for bone removal in CTA applies a hierarchical watershed transform as a preparation stage for both a support vector machine (SVM)-based automatic approach and an interactive editing step. Although the automatic processing time of the watershed implementation is fast (on average 20 seconds for a test dataset of 100 volumes), the quality is not satisfactory for a significant number of cases. FIG. 1 illustrates exemplary bone segmentation results of a CTA volume using various techniques. As illustrated in FIG. 1, image 100 shows a 3D visualization of an original CTA volume visualized using volume rendered technique (VRT). Image 110 shows a result of performing bone removal on the CTA volume 100 using the SVM-based watershed algorithm. As shown in image 110, a number of rib bones were not successfully removed by the SVM-based watershed algorithm. Another existing technique for automated bone removal in CTA feeds combined random shift intensity difference (RSID) features and landmark features into a probabilistic boosting tree (PBT) classifier. Although the PBT-based algorithm reaches an overall superior quality level with respect to the SVM-based watershed algorithm, the PBT-based algorithm is still problematic in some scenarios, such as in the thorax abdomen region. Image 120 of FIG. 1 shows a result of performing bone removal on the CTA volume 100 using the PBT-based algorithm. As shown in image 120, a kidney is missing and a rib was not removed using the PBT-based algorithm.

Embodiments of the present invention provide a deep learning based method for bone classification/segmentation and removal in CTA images. The deep learning based bone removal described herein achieves improved recognition quality as compared with the existing computer-based bone removal techniques described above. Image 130 of FIG. 1 shows a result of performing deep learning-based bone removal on the CTA volume 100 according to an embodiment of the present invention. As shown in image 130, the results of bone removal using the deep learning based method of the present invention is significantly improved as compared to the results 110 and 120 achieved using the existing methods. Embodiments of the present invention also provide various approaches to make the speed of the deep learning based bone classification reach similar performance to the existing techniques on a central processing unit (CPU).

Figure 2:
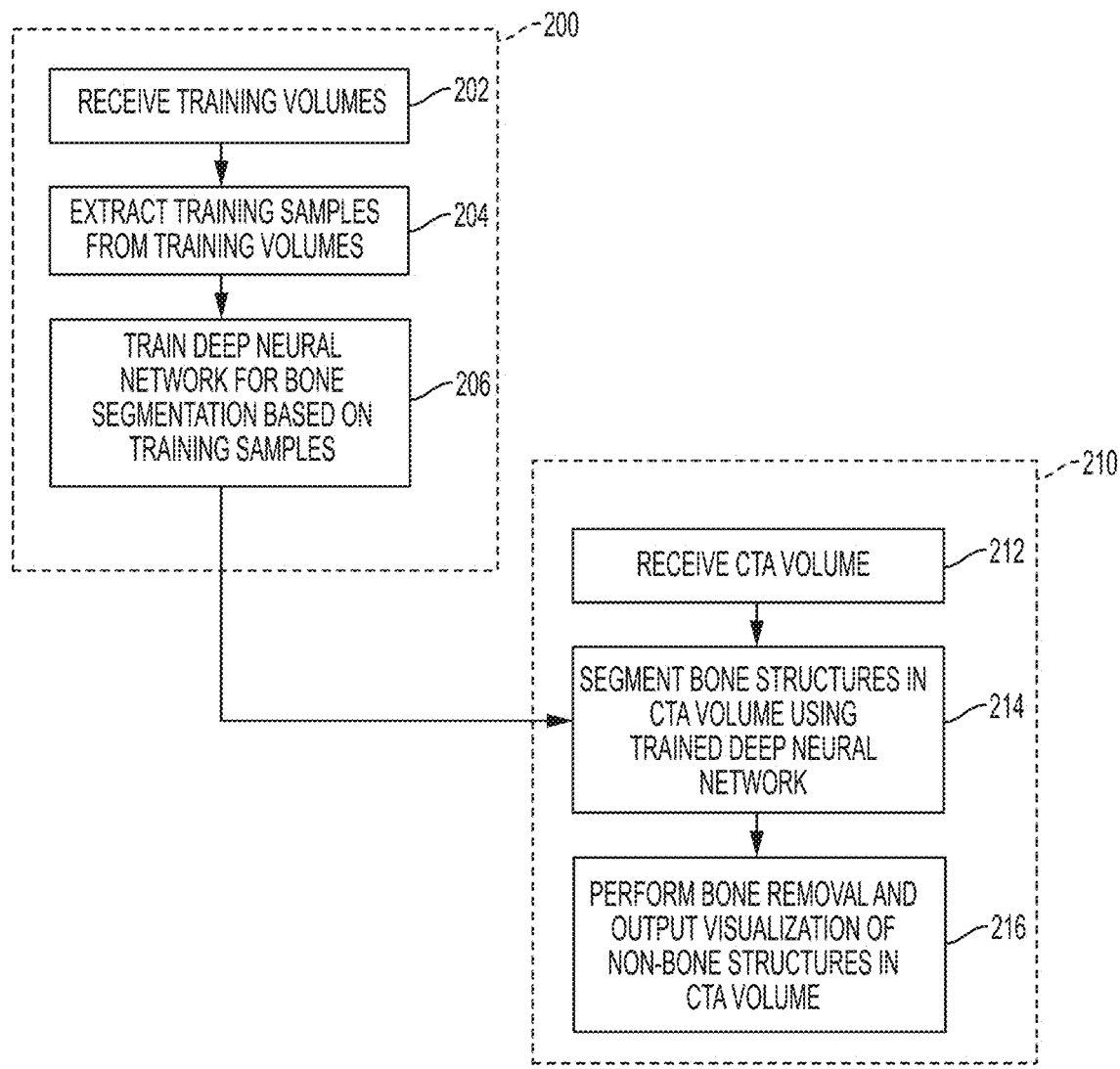
FIG. 2 illustrates a method for deep learning based bone removal in CTA images according to an embodiment of the present invention.

FIG. 2 illustrates a method for deep learning based bone removal in CTA images according to an embodiment of the present invention. The method of FIG. 2 includes a training stage 200 and an online bone removal stage 210. The training stage 200, which includes steps 202-206, is performed off-line to train a deep neural network (DNN) for bone segmentation/classification. The online bone removal stage 210, which includes steps 212-216, performs bone removal on a newly received CTA volume using the trained DNN resulting from the training stage 200. Once the DNN for bone segmentation/classification is trained in the training stage 200, the online bone removal stage 210 can be repeated for each newly received CTA image to perform bone removal on each newly received input CTA image using the trained DNN.

At step 202, training volumes are received. The training volumes can be 3D medical image volumes with annotated bone structures. In an advantageous implementation, the training volumes are CTA volumes with annotated bones structures. For example, the bone structures can be annotated manually by an expert. The training volumes can be received by loading stored training volumes from a database.

At step 204, training samples are extracted from each of the training volumes. Intensity thresholding is applied to each training volume to find voxels having intensities above a certain intensity threshold. For example, an intensity threshold of 123 Hounsfield units (HU), which is an intensity given by a transfer function of volume rendering technique (VRT). Positive (bone) and negative (non-bone) voxels that are above the intensity threshold are randomly sampled for each training volume. In an exemplary implementation, 2000 positive and negative voxels above the intensity threshold are randomly sampled from each training volume, but the present invention is not limited thereto. A training sample is generated for each of the sampled positive and negative voxels by extracting an image patch surrounding the voxel. In an advantageous implementation, a 19×19×19 image patch is extracted for each training sample.

At step 206, a deep neural network (DNN) for bone segmentation is trained based on the training samples. The DNN is trained to segment bone structures in a medical image (e.g., a CTA image) by classifying voxels in the medical image as positive (bone) or negative (non-bone). According to an advantageous embodiment, a deep convolutional neural network (CNN) can be trained for bone segmentation based on the training samples.

In recent years deep CNNs have enjoyed great success in image classification and other computer vision tasks. However, a major concern with applying CNNs lies in the expensive computations involved. With modern graphic processing units (GPU), CNNs have become a commodity in dealing with 2D RGB or gray-scale images in the computer vision field. However, in the medical imaging domain, especially for central processing unit (CPU)-based environments, an efficient implementation of 3D convolution is needed. Embodiments of the present invention described herein provide a deep CNN that reaches similar performance as the existing PBT-based solution in both runtime and memory consumption, while providing superior classification accuracy. In an advantageous embodiment of the present invention, a decomposed convolutional neural network, referred to herein as "BRDecompNet", is trained and used to perform bone segmentation. BRDecompNet reaches similar performance as the existing PBT-based solution in both runtime and memory consumption, while providing superior classification accuracy. A deep convolutional network, referred to herein as "BRNet" is described first followed by BRDecompNet, which is a decomposed version of BRNet.

BRNet

Convolutional networks typically involve stacking of multiple layers of convolution and non-linear mapping, and possibly down-sampling and deconvolution. The representative capacity is controlled by the depth and breadth of the network. Although a deeper and broader network is able to have more representative power, such a network requires a computationally expensive feed forward operation. According to an advantageous embodiment of the present invention, the present inventors have developed the BRNet network architecture to achieve a balance between complexity and efficiency.

Figure 3:
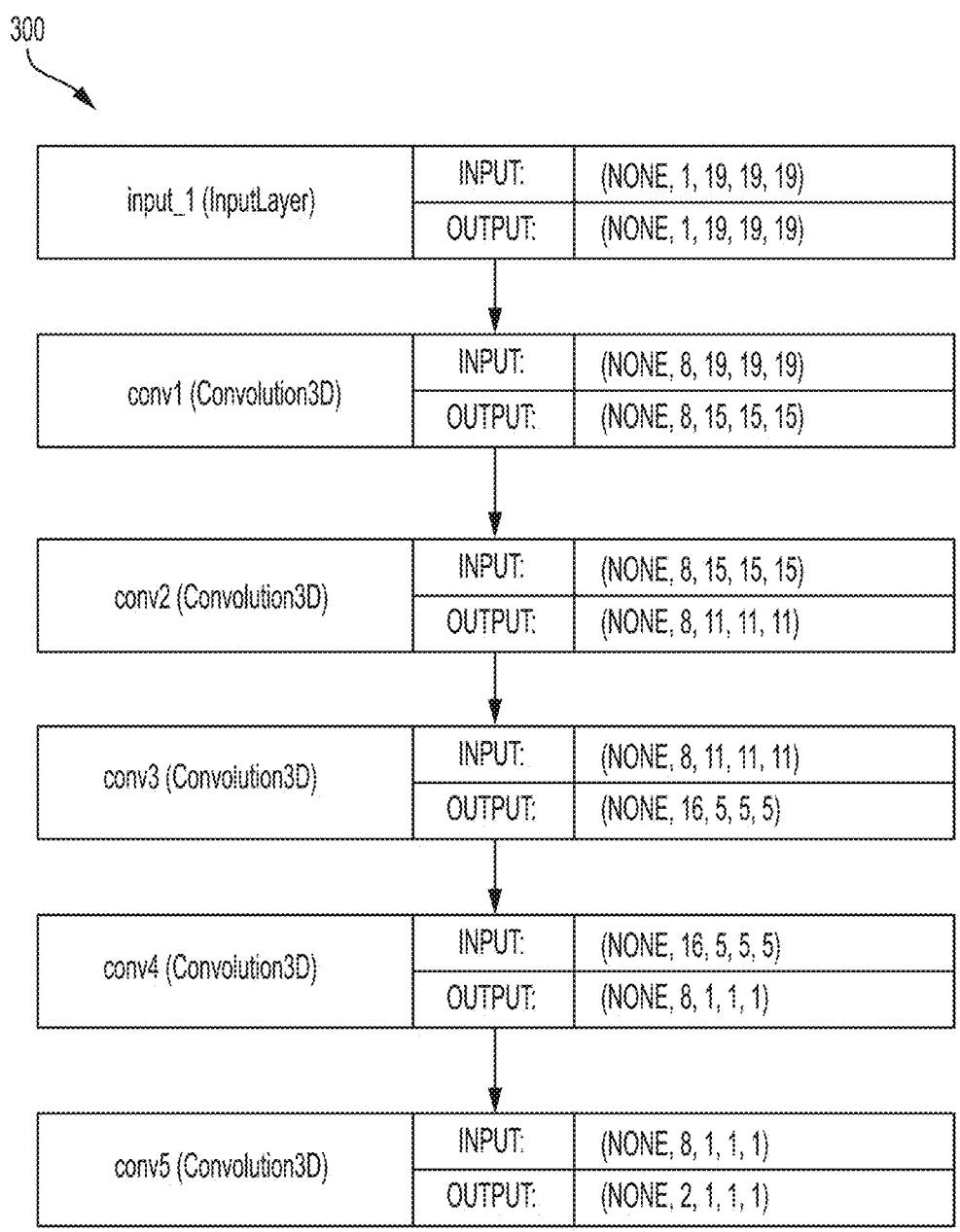
FIG. 3 illustrates a BRNet network architecture according to an embodiment of the present invention.

FIG. 3 illustrates the BRNet network architecture 300 according to an embodiment of the present invention. As shown in FIG. 3, BRNet 300 includes an input layer ("input_1") that inputs a 19×19×19 image patch of a CTA image. BRNet 300 further includes five convolutional layers ("conv1", "conv2", "conv3", "conv4", and "conv5"). Each of conv1, conv2, conv4, and conv5 includes eight feature maps, each applying a 5×5×5 filter on the image. Conv3 is the heaviest layer, which uses 16 feature maps with a 7×7×7 filter. Each convolutional layer is followed by a rectified linear unit (ReLu) nonlinear filter. A softmax layer is used after conv5. There is no down-sampling or up-sampling in the BRNet network 300 of FIG. 3.

Figure 5:
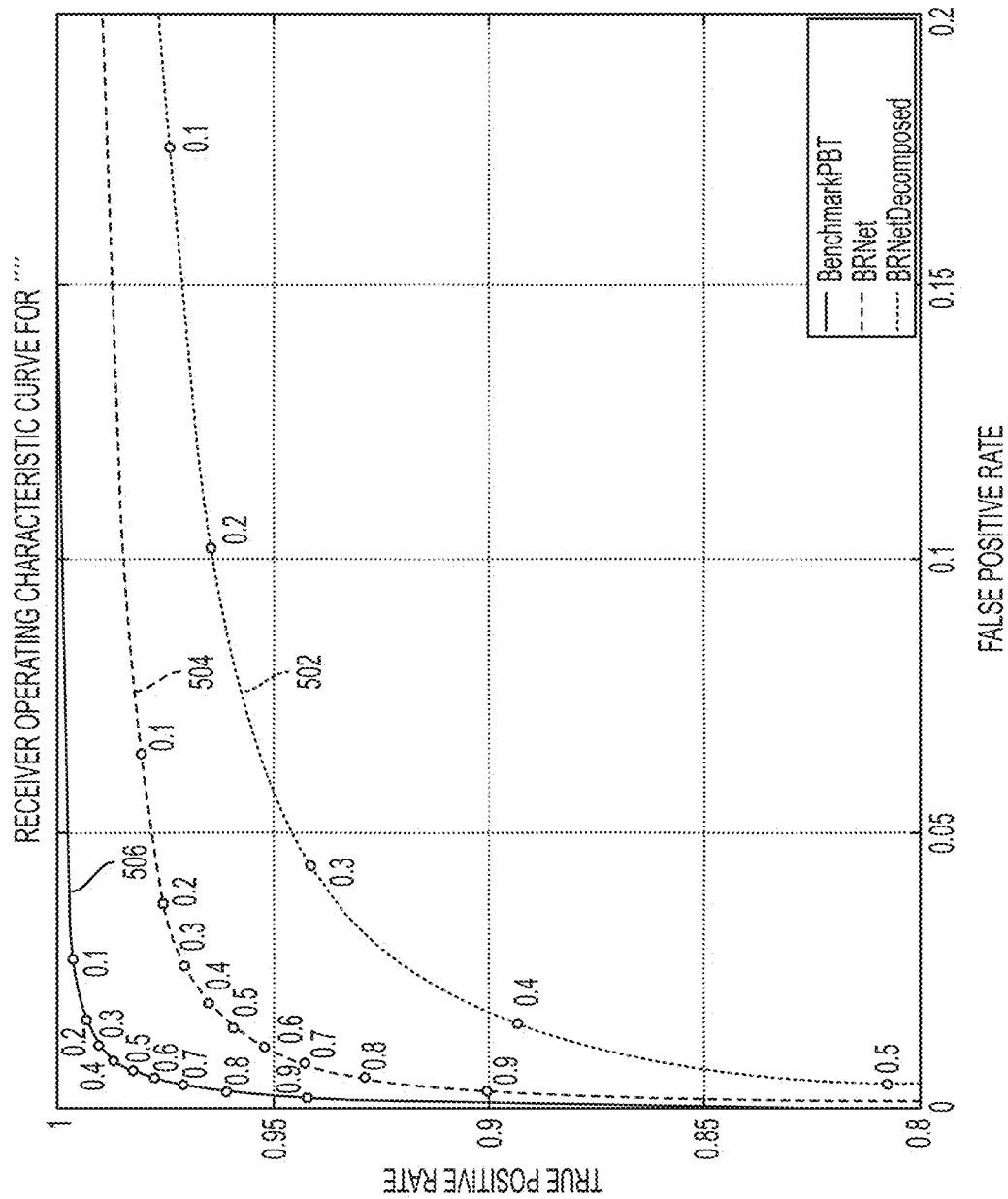
FIG. 5 illustrates a receiver operating characteristic (ROC) comparison of PBT, BRNet, BRDecompNet classifiers for bone segmentation.

The BRNet deep CNN is trained using the training samples extracted from the training volumes. Cross-entropy loss can be used during the training. Gradient descent and backpropagation can be used to find weights of the BRNet layers that minimize the cross-entropy loss of the network over all of the training samples. In an exemplary implementation by the present inventors, 48 training volumes were used to train the BRNet deep CNN. 2000 positive and negative voxels above the intensity threshold of 123 HU were sampled from each training volume and an image patch of 19×19×19, which is the input size of the network 300 of FIG. 3, was extracted for each training sample. BRNet results in improved accuracy, as compared to the existing PBT-based method, as shown in FIG. 5, which is discussed below. However, in the tests performed by the present inventors, BRNet required a longer runtime as compared with the existing PBT-based method and the existing SVM-based watershed method.

BRDecompNet: Decomposed Version of BRNet

In an advantageous embodiment, a decomposed version of BRNet, referred to herein as "BRDecompNet" can be trained for bone segmentation. 3D convolution is very slow. According to an advantageous embodiment, convolutional layers in BRNet can be decomposed into three light-weighted convolutional layers that respectively perform the convolution for each dimension. For example, conv3 of BRNet requires 16 convolutions with 8×7×7×7 4D kernel. In the BRDecompNet architecture, this heavy convolution is replaced with three light-light weights convolutional layers, which are composed of 16×8×7×1×1, 16×16×1×7×1, and 16×16×1×7, respectively. This reduces the number of weights, as well as the number of multiplication operations needed from 43904 to 4480 (bias is not counted for simplicity). Without loss of generality, let $N_p$ denote the number of feature maps in the previous layer. $N_c$ denotes the number of feature maps in the current layer. The kernel size of the original network is assumed to be $N_x$, $N_y$, $N_z$. Such a convolutional layer requires $N_c N_p N_x N_y N_z$ weights as well as multiplication operations. For the decomposed module, if $N_p$ is applied to each of the decomposed layers, the number of weights is $(N_c N_p N_x + N_p N_p N_y + N_p N_p N_z)$, which typically results in one magnitude of order less weights and multiplication operations. Following, this methodology for decomposing convolution layers, BRNet is decomposed into BRDecompNet.

Figure 4:
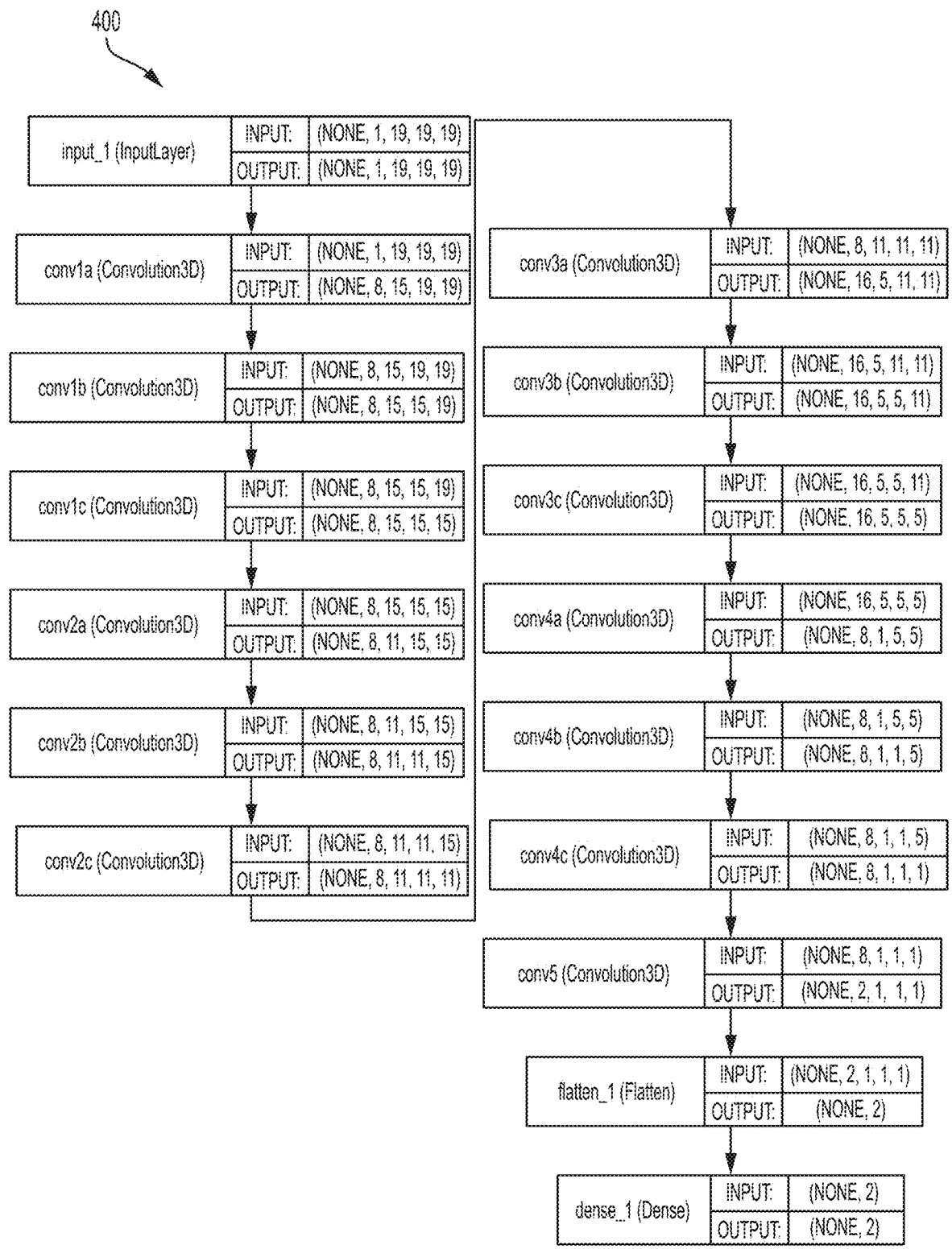
FIG. 4 illustrates a BRDecompNet architecture according to an embodiment of the present invention.

FIG. 4 illustrates the BRDecompNet architecture 400 according to an embodiment of the present invention. As shown in the BRDecompNet architecture 400 of FIG. 4, conv1, conv2, conv3, and conv4 from BRNet are each decomposed into three light-weight convolutional layers that perform convolution for each dimension. In particular, conv1 in the BRNet architecture 300 of FIG. 3 is decomposed into conv1a, conv1b, and conv1c in the BRDecompNet architecture 400 of FIG. 4. Conv2 in the BRNet architecture 300 of FIG. 3 is decomposed into conv2a, conv2b, and conv2c in the BRDecompNet architecture 400 of FIG. 4. Conv3 in the BRNet architecture 300 of FIG. 3 is decomposed into conv3a, conv3b, and conv3c in the BRDecompNet architecture 400 of FIG. 4. Conv4 in the BRNet architecture 300 of FIG. 3 is decomposed into conv4a, conv4b, and conv4c in the BRDecompNet architecture 400 of FIG. 4. Conv5 remains the same in the BRDecompNet architecture 500, resulting a total of 13 convolutional layers. Conv5 is followed by a flatten layer ("flatten_1"), which flattens the output of conv5 into a 1D feature vector, and a dense layer ("dense_1"), which outputs a classification result the classifies a voxel as positive (bone) or negative (non-bone).

The BRDecompNet deep CNN is trained using the training samples extracted from the training volumes in a similar manner to the BRNet network. Cross-entropy loss can be used during the training. Gradient descent and backpropagation can be used to find weights of the BRDecompNet layers that minimize the cross-entropy loss of the network over all of the training samples. In an exemplary implementation, for evaluation purposes, the same training and testing dataset was used for the BRDecompNet as the BRNet. In another exemplary implementation, a final BRDecompNet version was trained based on a training set of 84 volumes, with 8,000 positive and negative samples respectively extracted from each training volume. BRDecompNet achieves approximately 80% reduction in computation time, as compared to BRNet.

Figure 6:
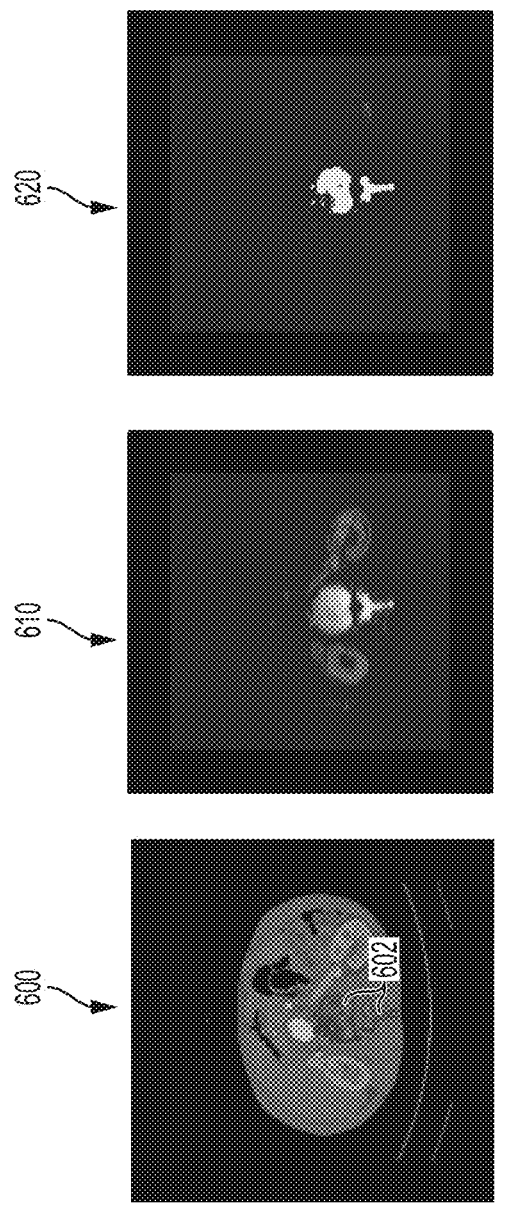
FIG. 6 illustrates a comparison of probability maps generated using a PBT classifier and a BRDecompNet deep CNN classifier.

In tests performed by the present inventors, BRDecompNet achieved 98.5% classification accuracy for bone segmentation on a test data set that included 20 thorax abdomen cases, compared to 93.2% classification accuracy of the existing PBT-based solution. The evaluation of the final VRT view resulting from bone removal using BRDecompNet on 100+ tested unseen volumes also proved to have better quality than both the existing SVM-based watershed approach and the existing PBT-based approach. FIG. 5 illustrates a receiver operating characteristic (ROC) comparison of the PBT, BRNet, BRDecompNet classifiers for bone segmentation. FIG. 5 shows the ROC curves for the PBT 502, BRNet 504, and BRDecompNet 506 for the 20 thorax abdomen volumes, with the corresponding probability threshold ranging from 0.1 to 0.9. As one example, applying the probability threshold of 0.5 on the PBT results in about 1% false positive rate and 81% true positive rate, while the same probability threshold on BRDecompNet results in about 1% false positive rate and 98% true positive rate. FIG. 6 illustrates a comparison of probability maps generated using the PBT classifier and the BRDecompNet deep CNN classifier. As shown in FIG. 6, image 600 is an original CTA image overlaid with an annotated mask 602 as ground truth, image 610 is a probability map resulting from bone segmentation using a trained PBT classifier, and image 620 is a probability map resulting from bone segmentation using a trained BRDecompNet deep CNN classifier. As can be observed in FIG. 6, the probability map 610 resulting from bone segmentation using the PBT includes many false positives in the renal artery and kidney, while the false positives are largely absent in the probability map 620 resulting from bone segmentation using the BRDecompNet.

Bone segmentation and removal using BRDecompNet improves the classification accuracy as compared to the existing PBT-based method. Various embodiments of the present invention are described herein that make BRDecompNet reach similar performance as the existing PBT solution on a CPU, both in terms of runtime and memory consumption. Table 1 shows a comparison of runtime and memory consumption of the existing PBT-based bone removal and the BRDecompNet deep learning-based bone removal on 100+ unseen testing volumes.

TABLE 1

|        | PBT RunTime (s) | BRDecompNet RunTime (s) | PBT Memory (MB) | BRDecompNet Memory (MB) |
|--------|-----------------|-------------------------|-----------------|-------------------------|
| Mean ± | 78.90 ±         | 81.29 ±                 | 1306.91 ±       | 1302.39 ±               |
| Stdev  | 63.96           | 66.96                   | 851.99          | 831.54                  |
| Max    | 310.5           | 321.8                   | 4483            | 4345                    |
| Min    | 12.3            | 12.2                    | 196             | 252                     |
| Median | 61.75           | 65.15                   | 1111            | 1119                    |
| 80%    | 108             | 111.2                   | 1967            | 1934                    |

BRFGNet: Filtered Grouped Version of BRNet

Figure 7:
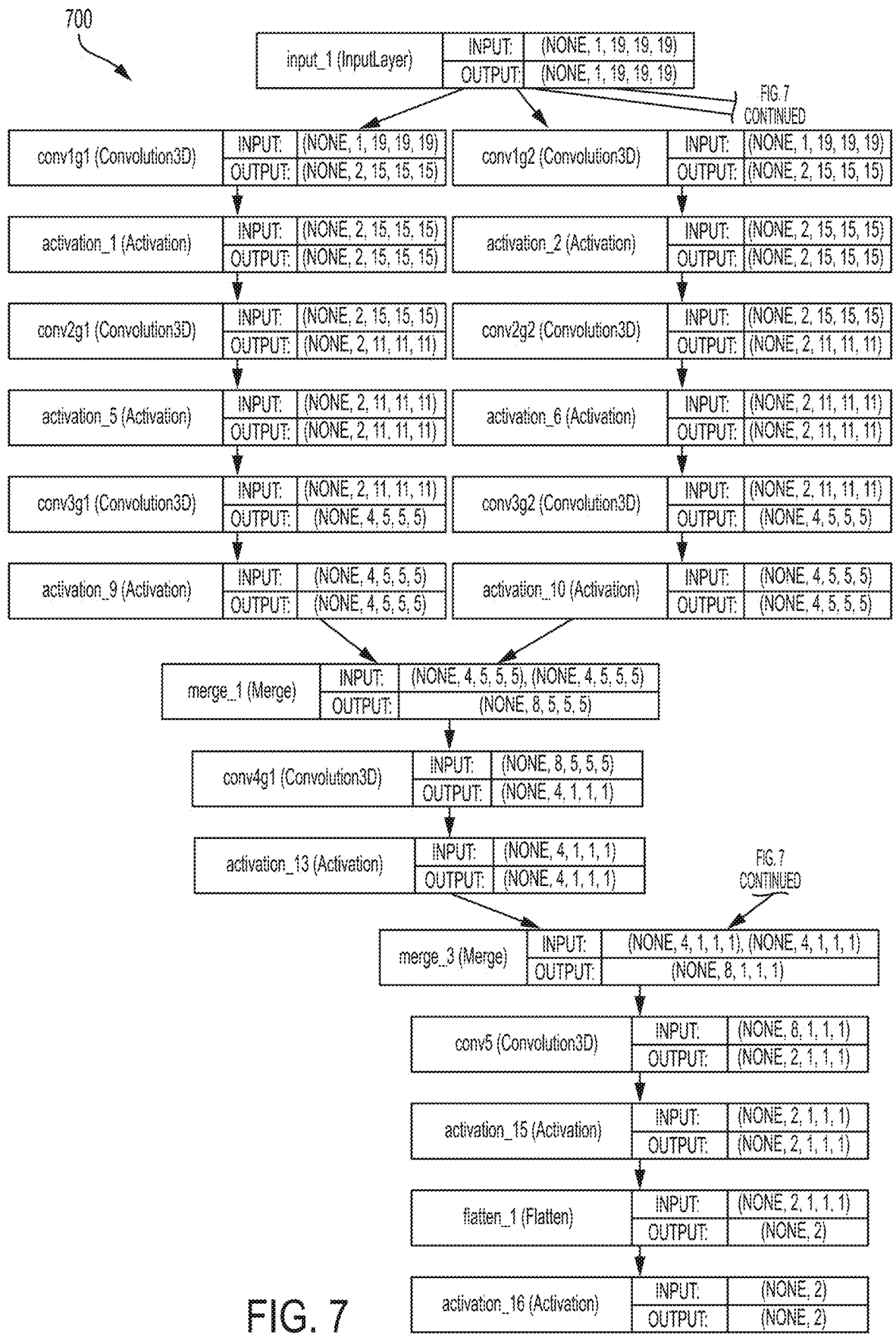
FIG. 7 illustrates a BRFGNet network architecture according to an embodiment of the present invention.
Figure 7:
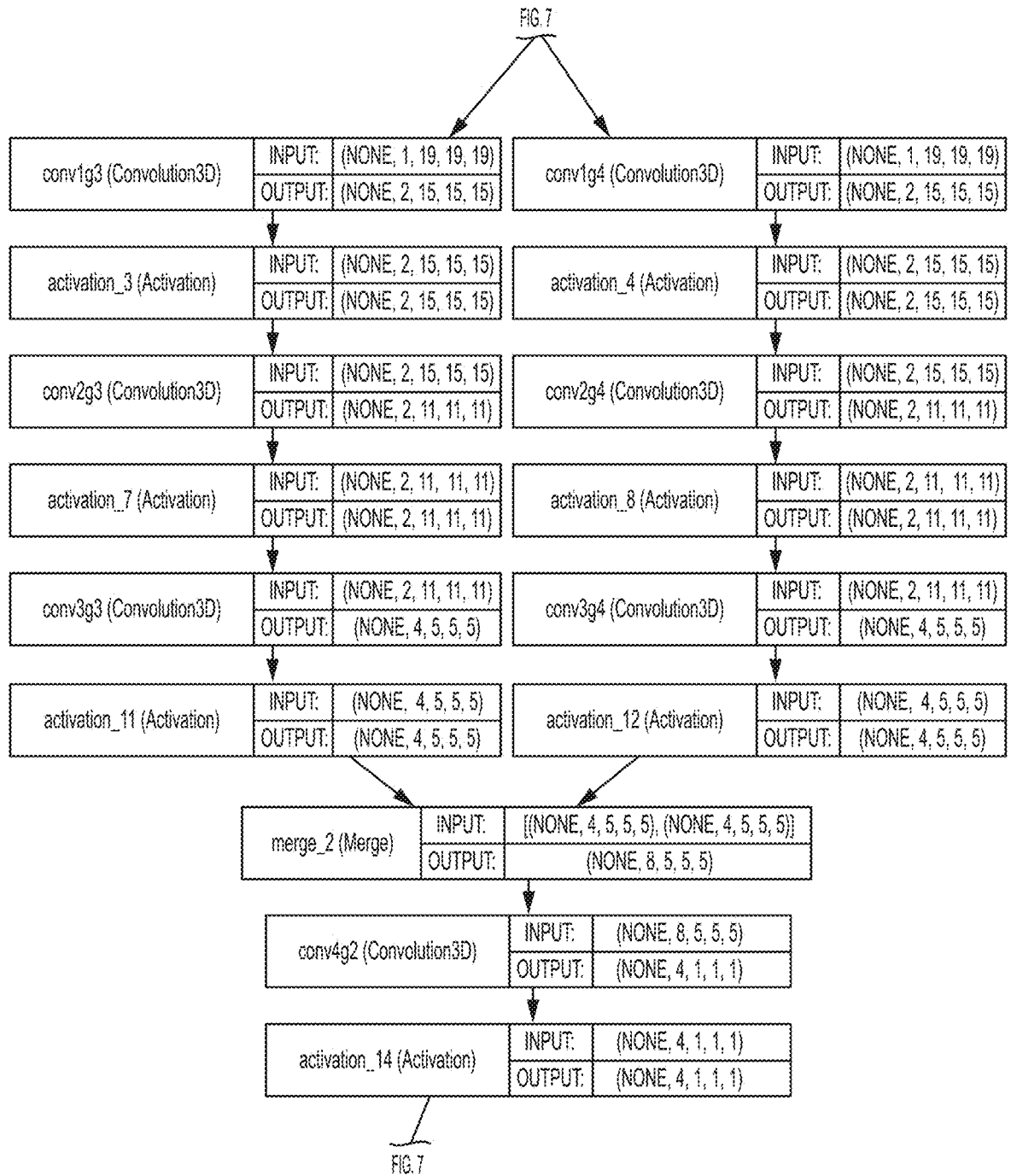

In another possible embodiment, a filtered grouped version of BRNet, referred to herein as "BRFGNet" can be trained for the deep learning based bone segmentation and removal. The motivation for using BRFGNet is to reduce the network size by convoluting with only subset of feature maps in the previous layer. FIG. 7 illustrates a network architecture 700 of BRFGNet according to an embodiment of the present invention. As shown in FIG. 7, in the BRFGNet architecture 700, conv1, conv2, and conv3 in the BRNet architecture 300 of FIG. 3 are each divided into four groups and conv4 in the BRNet architecture 300 of FIG. 3 is divided into two groups. In particular, conv1 is divided into "conv1g1", "conv1g2", "conv1g3" and "conv1g4" in the BRFGNet architecture 700. Conv2 is divided into "conv2g1", "conv2g2", "conv2g3" and "conv2g4" in the BRFGNet architecture 700. Conv3 is divided into "conv3g1", "conv3g2", "conv3g3" and "conv3g4" in the BRFGNet architecture 700. Conv4 is divided into "conv4g1" and "conv4g2" in the BRFGNet architecture 700. There are two merge operations ("merge_1" and "merge_2") before conv4g2 and conv4g2 to merge the four output feature vectors into two. Another merge operator ("merge_3") before conv5 merges two output feature vectors into one. Multiple variances of filter-grouped networks can be trained including ones using decomposed features.

Returning to FIG. 2, once the DNN (e.g., BRDecompNet, BRNet, BRFGNet) is trained in step 206, the trained DNN is stored, for example on a memory or storage device of a computer system, and can then be used in the online bone removal stage 210 to segment bone structures in newly received CTA volumes. The online bone removal stage 210 includes steps 212-216.

At step 212, a CTA volume of a patient is received. The CTA volume can be a CTA volume of a specific region of the patient's body or can be whole body CTA volume acquired using a whole body scan of the patient. The CTA volume of the patient can be received directly from a CT scanner, or the CTA volume of the patient can be received by loading a CTA volume previously stored on a memory or storage of a computer system or receiving the CTA volume via a network transmission from another computer system.

Although a CTA image is received and bone removal is performed on the CTA volume in the method of FIG. 2, the present invention is not limited to a CTA volume and the method of FIG. 2 can be similarly applied to other types of medical images/volumes, as well. For example, the method of FIG. 2 can be similarly performed on 3D or 2D medical image data of the patient acquired using various imaging modalities such as computed tomography (CT), combined positron emission tomography (PET)-CT, as magnetic resonance imaging (MRI), ultrasound, etc.

At step 214, bone structures are segmented in the CTA volume using the trained deep neural network (DNN). As described above, the trained DNN can be a deep CNN trained for bone segmentation. In an advantageous embodiment, the trained BRDecompNet deep CNN is used to segment the bone structures in the CTA volume. In other possible embodiments, the BRNet deep CNN or the BRFGNet deep CNN can be used for the bone segmentation. The trained deep neural network (e.g., BRDecompNet) segments bone structures in the CTA volume by classifying voxels in the CTA image as bone voxels (positive) or non-bone voxels (negative). In a possible implementation, for a given voxel in the CTA volume the trained DNN inputs a predetermined sized image patch surrounding the voxel and outputs a classification result (i.e., bone or non-bone) for the voxel. The size of the image patch corresponds to the size of the input layer in the trained DNN architecture. In an exemplary implementation, image patches of size 19×19×19 voxels can be input to the trained DNN, but the present invention is not limited thereto.

In an exemplary embodiment, a C++ implementation can be used to perform the segmentation by the trained DNN. Various embodiments provided herein for implementing the deep learning based bone segmentation by the trained DNN improve the speed and memory usage of the deep learning based segmentation. In an advantageous implementation, end-to-end convolution is performed. During the training of BRDecompNet, the training volumes are sampled in 19×19×19 image patches. However, if patch-wise convolution is used during the online bone removal stage, there are many unnecessary repetitive convolutions on proximate samples. Accordingly, in an advantageous implementation, instead of repeatedly inputting image patches classification results for individual voxels and utilizing the fact that convolution operations are of spatial nature, the trained DNN can perform end-to-end convolution in which each layer of the trained DNN computes the feature maps for all of the voxels to be classifier and the trained DNN outputs a probability map or mask that provides the classification results for all of the voxels.

In another advantageous implementation, convolution is performed on masked voxels. For CTA bone removal, not all voxels are needed for classification, since voxels with intensities lower than 123 HU are skipped for rendering. Accordingly, in an advantageous implementation, convolution only needs to be computed for voxels with intensities above 123 HU. In this case, intensity-based thresholding can be performed in the CTA volume prior to applying the trained DNN. This allows the trained DNN to only consider sufficiently bright voxels whose intensities are above an intensity threshold (e.g., 123 HU). This intensity thresholding results in a thresholded mask. Given a receptive field for BRDecompNet of 19×19×19, a dilation of 19×19×19 kernel is performed on the thresholded mask. Typically, only about 6% of the voxels of an entire CTA volume have an intensity above 123 HU. By performing the dilation, a speed gain of 40% is achieved by performing the convolution on the masked voxels.

Figure 8:
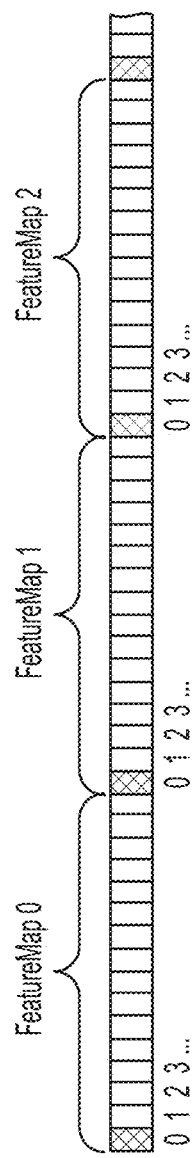
FIG. 8 illustrates an example of memory allocation for convolution on 1D data.

In another advantageous implementation, the memory allocation for the trained DNN can be made to be more contiguous. For 3D convolution, typically a 4D data tensor is used during the feed forward operation, with channel as the additional dimension. A 5D convolutional kernel is used, with the number of feature maps in the previous layer, as well as the number of feature maps in the next layer as additional two dimensions. Typically, the 4D data tensor is stored in order of CZYX, with kernel tensor stored in NCZYX, where N and C is the number of feature maps in the next and previous layer, respectively. During the convolution, this order might bring slowdown, since the memory access is not contiguous in the channel. For simplicity sake, FIG. 8 illustrates an example of memory allocation for convolution on 1D data. Here, the order of CX is used for the data tensor, and NCX is used for the kernel tensor. It can be seen in FIG. 8 that, in order to perform one convolution operation, the memory needs to jump every $N_x$ slot to access the same image index location (0, 1, 2, 3, . . . ) in the next feature map (FeatureMap 0, FeatureMap 1, FeatureMap 2) where $N_x$ is the dimension of the feature map size. The compiler favors contiguous memory access. According to an advantageous implementation, the NCZYX order can be changed to NZYXC, where the feature values of all the channels corresponding to the same feature map are indexed together. The present inventors have observed up to a 25% speed improvement by changing the NCZYX order to NZYXC, where the feature values of all the channels corresponding to the same feature map are indexed together.

In another advantageous implementation, 2D slices can be allocated to columns of an image matrix used for the convolution instead of 3D images. The convolution involves matrix multiplication $M_I \cdot M_k \cdot M_I$ is referred to herein as the "image matrix", which is a $N_s \times N_c \times N_x \times N_y \times N_z$ matrix, where $N_s$ is the number of columns (samples), $N_c$ is the number of channels in the previous layer, and $N_z$, $N_y$, and $N_x$ are the kernel dimension in Z, Y and X, respectively. In many public deep learning libraries, like Caffe, $N_s$ is typically all the samples in the image. This is not a problem for a 2D image. But for BRDecompNet, assuming that convolution is performed on a 200×160×160 volume and 6% voxels are above 123 HU, the number of voxels after 19×19×19 dilation that need to go through convolution is 30%. The memory needed to store one feature $M_I$ for the second 1×5×1 convolution layer is therefore 200×160×160×0.3×8×1×5×1×4=246 MB (without masking, it is 819 MB). For the non-decomposed BRNet, it is 200×160×160×0.3×8×5×5×5×4=6 GB (20 GB without masking). These memory requirements may be too large to be practical, since this is just a previous layer and a second buffer is also needed to store the next layer. Alternatively, in an advantageous implementation, $M_I$ is allocated slice-by-slice, which greatly reduces $N_s$. Accordingly, this embodiment provides special handling for 3D volumetric medical image data in order to reduce the memory consumption required for the convolution of the 3D volumetric medical image data.

In another advantageous implementation, a library, such as Integrated Performance Primitives (IPP) and Math Kernel Library (MKL) can be used. Libraries, such as IPP and MKL, provide optimized functions for matrix multiplication with low-level vectorization and Single Instruction Multiple Data (SIMD) instructions. The use of IPP or MKL functions together with the contiguous NZYXC memory ordering provides 40% increase in speed of the segmentation using the trained DNN.

Figure 9:
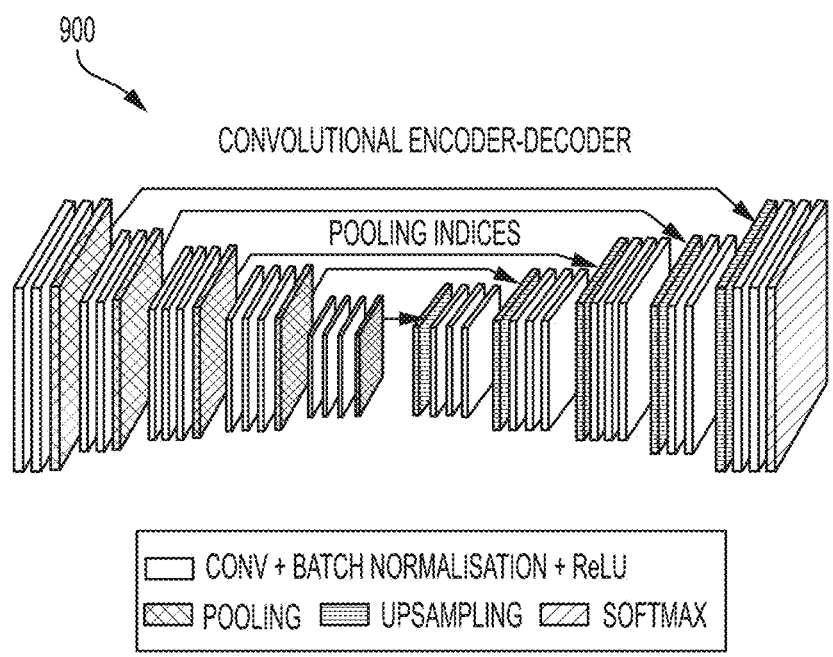
FIG. 9 illustrates an exemplary architecture of a deep convolutional encoder-decoder (CED)

Returning to FIG. 2, at step 216, bone removal in the CTA volume is performed and non-bone structures in the CTA volume are visualized. A 3D visualization of the CTA volume is generated using VRT. The segmented bone structures are removed from the 3D visualization of the CTA volume. The bone structures can be removed from the 3D visualization of the CTA volume by setting the intensity of voxels classified as bone voxels in the CTA image to zero. Once the bone structures are removed, the 3D visualization of the CTA image provides a 3D visualization of the non-bone structures (e.g., vascular structures) in the CTA image. The 3D visualization of the non-bone structures in the CTA image can be displayed, for example on a display device of a computer system. Image 130 of FIG. 1 shows a 3D VRT visualization of non-bone structures resulting from performing deep learning-based bone removal on the CTA volume 100 using the BRDecompNet deep CNN according to an embodiment of the present invention In the embodiments described in connection with the method of FIG. 2, the trained DNN is a deep CNN (e.g., BRNet, BRDecompNet). In an alternative embodiment, the DNN for bone segmentation can be trained by end-to-end training of a deep convolutional encoder-decoder (CED). FIG. 9 illustrates an exemplary architecture 900 of a deep CED. Two major differences between the deep CED 900 and the BRNet/BRDecompNet architectures described above are: (1) The downsampling and upsampling layers in the deep CED 900 an significantly increase the receptive field, thus more contextual information can be used; and (2) The deep CED 900 is trained in an image-to-image way, such that there is no need to do random sampling on a subset of samples.

Deep-Image-to-Image Network with Multi-Task Learning

In another embodiment of the present invention, a deep image-to-image network (DI2IN) trained using multi-task learning (MTL) can be used to perform bone segmentation and bone removal in a CTA volume. The trained DI2IN (described in greater detail below) can be used as the trained DNN in the method of FIG. 2. In a possible implementation, a bone mask generated by the trained DI2IN can be used by itself to perform the bone removal in step 216 of FIG. 12. In another possible implementation, the bone mask generated by the trained DI2IN can be used together an aorta mask and a vessel mask to generate a final mask for bone removal using the method shown in FIG. 10.

Figure 10:
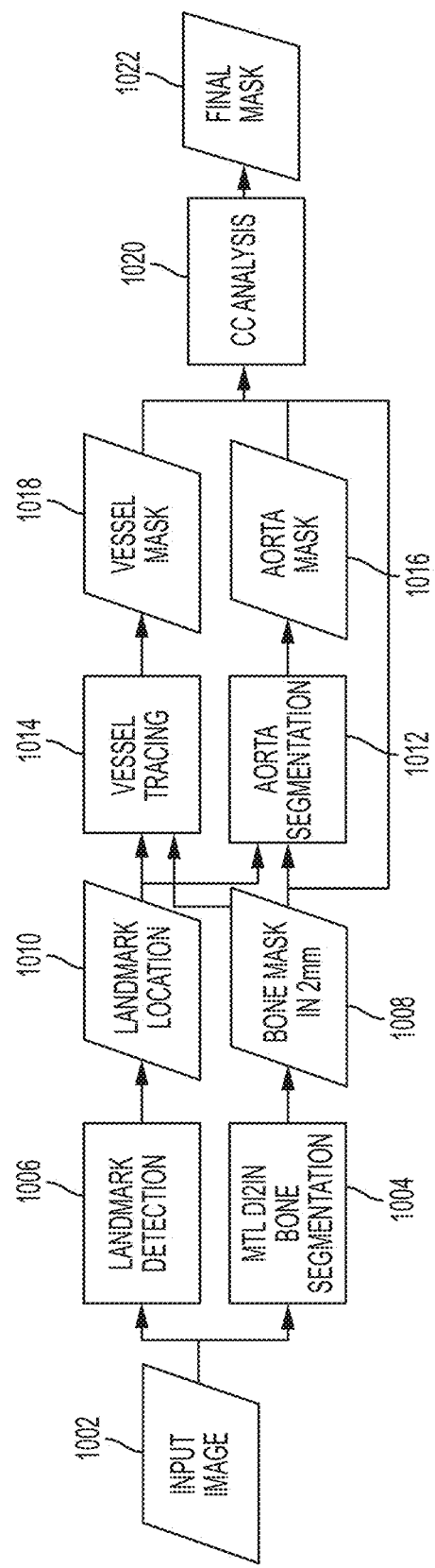
FIG. 10 illustrates a method for bone removal in a CTA volume using a deep image-to-image network (DI2IN) and multi-task learning (MTL) according to an embodiment of the present invention.

FIG. 10 illustrates a method for bone removal in a CTA volume using a DI2IN and MTL according to an embodiment of the present invention. As illustrated in FIG. 10, an input image 1002 is received. In exemplary embodiment the input image 1002 is a CTA volume. The input CTA volume 1002 may be received directly from an image acquisition device (i.e., a CT scanner) or may be received by loading a previously acquired CTA volume. In the color mapping of 3D volume rendering, only voxels with intensities higher than a certain intensity threshold τ are displayed. For a given CTA volume V, the method of FIG. 10 only needs to determine labels for voxels $v \in V_h$, where $V_h = \{v | I(v) > \tau\}$. Accordingly, intensity thresholding can be applied to remove voxels with intensities less than the intensity threshold x (e.g., τ=123 HU) prior to applying the DI2IN. Referring again to FIG. 10, DI2IN trained using MTL is used to perform bone segmentation 1004 and landmark detection 1006 in the input image 1002. DI2IN, MTL, bone segmentation 1004 and landmark detection 1006 are described in greater detail below. The bone segmentation 1004 results in a bone mask 1008. The landmark detection 1006 results in landmark locations 1010. The bone mask 1008 and landmark locations 1010 are used to perform region-growing based aorta segmentation 1012 and vessel tracing 1014. The region-growing based aorta segmentation 1012 results in an aorta mask 1016 and the region-growing based vessel tracing 1014 results in a vessel mask 1018. A connected component (CC) analysis 1020 is then performed based on the bone mask 1008, the aorta mask 1016 and the vessel mask 1018 to generate a final mask 1022 used for bone removal in the input image. Methods for performing the region-growing based segmentation/vessel growing and the CC analysis for generating the final mask are described in greater detail in United States Publication No. 2016/0328855, filed May 4, 2015 and entitled "Method and System for Whole Body Bone Removal and Vascular Visualization in Medical Image Data", the disclosure of which is incorporated herein in its entirety by reference.

In CT(A) volumes, a 3D convolution kernel has the advantages of utilizing more contextual information, comparing to a 2D counterpart. However, a 3D DI2IN would have to be trained from scratch, since no pre-trained network that sees millions of examples is available. Insufficient training data may result in poor generalization for such a 3D DI2IN. In an advantageous embodiment of the present invention, one unified network (DI2IN) is used to learn both bone segmentation and body landmark detection, where the later is an auxiliary task, with the goal to improve generalization of learning of the primary task of bone segmentation. Reasons for applying such transfer learning/MTL strategy include: (1) Both tasks can be formulated by DI2IN in the same resolution (e.g. 2 mm), where common features are shared; (2) The number of volumes with annotated landmark is much larger than volumes with annotated bone. This enables the MTL network to see more training images; and (3) The bone shape has very high correlation with body region.

Equation (1) shows the general MTL framework that the present inventors have adapted to the application of bone segmentation. For every task t∈{1, ... T}, there are $N_t$ training data $x_i^t$ and label $y_i^t$, while i∈{1, ... $N_t$}. $f(x_i^t; w^t)$ is a function of $x_i^t$ and parameterized by a weight vector $w^t$. The summation takes the loss function $\mathcal{L}$ and weight regularization term $\Phi_t(w^t)$. $\lambda_t$ is the importance coefficient of task t's cost. It can be noted that in the present application, both the data and the loss function can be different among the tasks. This feature gives better flexibility in dealing with different tasks and datasets.

$$\arg\min_{\{w^t\}_{t=1}^T} \sum_{t=1}^T \left( \lambda_t \sum_{i=1}^{N_t} \mathcal{L}_t(y_i^t, f_t(x_i^t; w^t)) + \Phi_t(w^t) \right), \quad (1)$$

Equation (1) can be expanded as:

$$\arg\min_{\{w_b, w_r\}} \Sigma_{i=1}^{N_b} \mathcal{L}_b(y_i^b, f_b(x_i^b; w^b)) + \lambda_r \Sigma_{i=1}^{N_r} \mathcal{L}_r(y_i^r, f_r(x_i^r; w^r) \quad (2)$$

where b and r are used to denote bone segmentation and landmark detection, respectively. Regularization terms are omitted from Equation (2) for simplicity.

DI2IN trains a deep neural network that performs a mapping of an input image to an output image. For the bone segmentation task, a medical image volume, such as a CTA volume is input to the DI2IN and the DI2IN outputs an image in which for each voxel a probability value is given to represent the likelihood of being bone or not. The negative-log likelihood loss for the last output layer is as follows:

$$L_b(y_i^b, f_b(x_i^b; w^b)) = \frac{1}{\mathcal{N}(M(x_i^b))} \sum_{x_b \in x_i^b} (-\log(f_b(x_i^b, w^b)) M(x_i^b)) \quad (3)$$

where $\lambda_{reg}^b$ is the weight of the regularization term and N represents the function of counting the number of non-zero voxels. The use of the masking function M(v)=ψ(I(v)>τ) (ψ is a binary step function) guarantees that the backpropagation used to train the DI2IN for bone segmentation only occurs for $V_h = \{v | I(v) > \tau\}$. During the testing stage, the probability value from $v \notin V_h$ is set to zero after the DI2IN feed forward operation. Alternatively, M(v) can be also reformatted into a weighting function to balance the biased distribution of bone and vessel in some body regions.

In an advantageous implementation, the auxiliary task aims to detect eight body landmarks: including carina bifurcation, left and right kidney center, left and right hip bone, brachiocephalic artery bifurcation, left common carotid artery and left subclavian artery. Those landmarks are present in different regions of the body. Those landmarks are first used to generate heat maps with Gaussian blobs that are centered at their locations in the training images. The width of the Gaussian function is empirically determined. To cope with the sparsity of the positive landmark heat value in the map, mean square error metric is used as the loss function in equation (4), where $y_i^r$ is the ground truth heat map.

$$L_r(y_i^r, f_r(x_i^r; w^r)) = \frac{1}{\mathcal{N}(x_i^r)} \sum_{x_i \in x_i^r} \|f_r(x_i^r, w^r) - y_i^r\|^2. \quad (4)$$

Figure 11A:
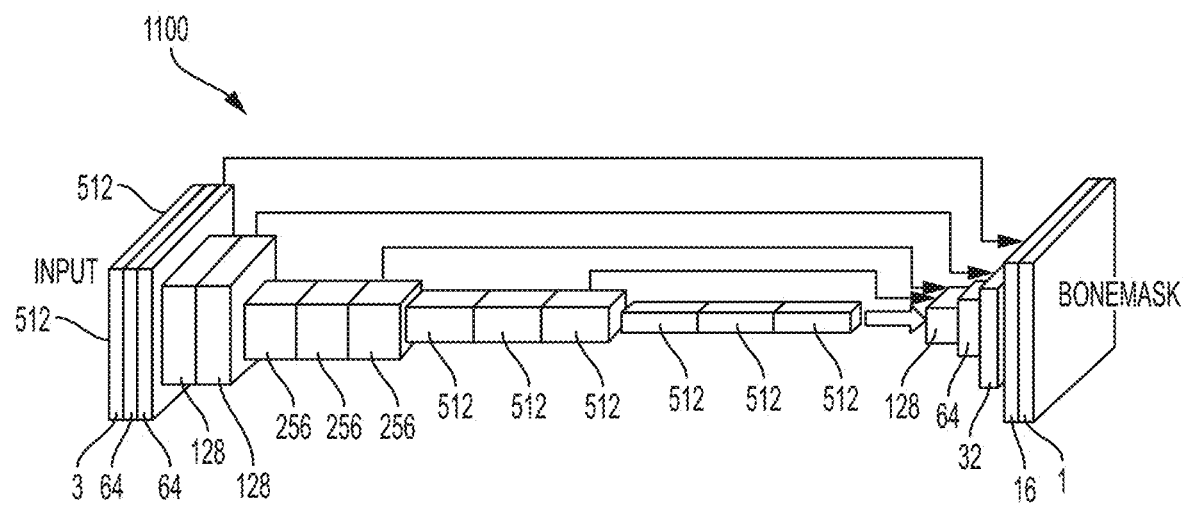
FIGS. 11A and 11B illustrate exemplary network architectures for a 2D DI2IN and a 3D MTL DI2IN, respectively.
Figure 11B:
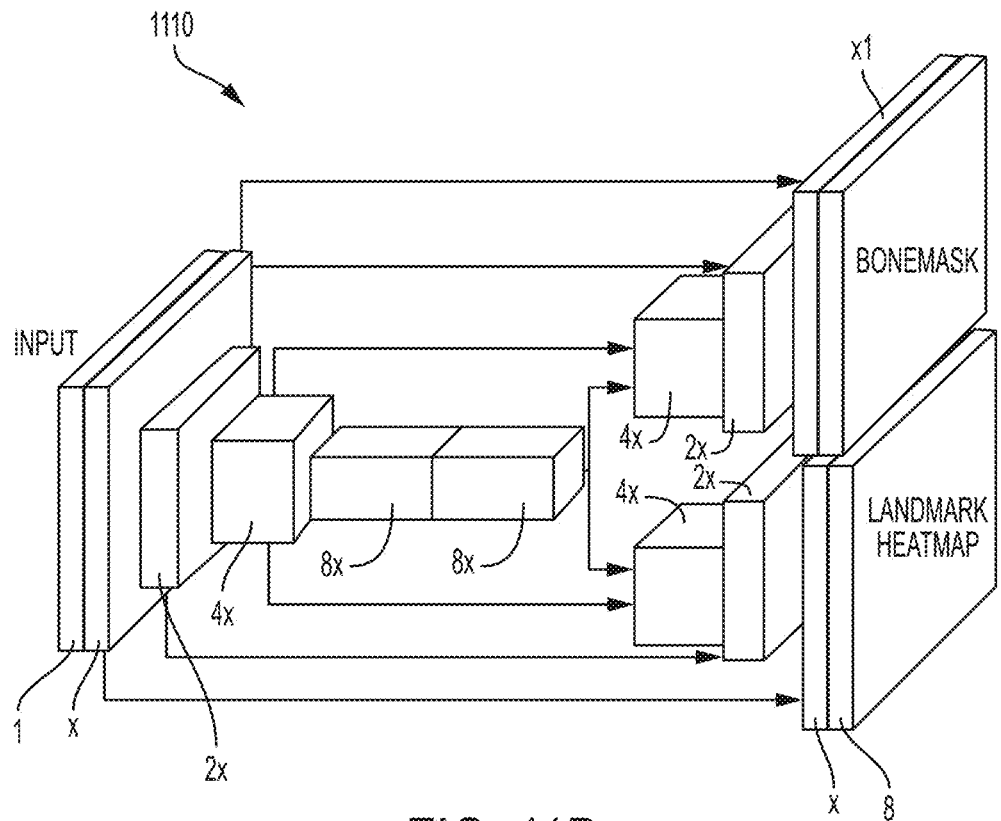

FIGS. 11A and 11B illustrate exemplary network architectures for a 2D DI2IN and a 3D MTL DI2IN, respectively. As shown in FIG. 11B, the 3D MTL DI2IN architecture 1110 is branched into two parts for each task (bone segmentation and landmark detection), where $w_b$ and $w_r$ in equation (2) share common weights. In both transfer and multi-task learning, only those weights are shared or transferred across tasks. The two branched decoding paths corresponding to the two tasks only differ in the last non-linear layer output. The cross entropy loss of the bone segmentation and mean square loss of the landmark heatmap is handled by Sigmoid and ReLu layers, respectively. The shortcut connections from layers of equal resolution in the encoding path provides essentially high resolution features to the decoding path. It is to be understood that 4D tensors are displayed as 3D for simplicity here in FIG. 11B. FIG. 11A shows the DI2IN architecture 1100 used for 2D bone segmentation. The 2D DI2IN architecture 1100 has similar architecture with deep CED, and can be loaded with pre-trained VGG weights. Overall, the 2D network 1100 has 16 M parameters, corresponding to about 64 MB disk size. The 3D MTL network 1110 has 293 K parameters and corresponds to 1.15 MB disk size.

In an exemplary implementation, a total of 1090 3D CTA volumes with bone annotation, which cover a variety of different body regions, kV range, fields of view, reconstruction kernels, slice thickness, patient age and pathologies, were used for training the MTL DI2IN. All those 3D CTA volumes have 2D axial slice dimension of 512×512, with a resolution ranging from 0.4 mm to 0.7 mm. The slice thickness ranges from 0.4 mm to 5 mm. Among those data, 123 volumes are fully annotated in resampled 2 mm resolution, while the remaining 967 volumes are annotated in sparse 2D slices at an original resolution. The landmark heat map regression is based on a set of 2467 3D CT volumes, which are all resampled to 2 mm. Both of the bone and landmark annotations were made by 10 medical students and were at least reviewed and corrected for two times.

In the experiments run by the present inventors, the data is randomly shuffled and split into 75% for training and 25% for testing. The training was performed using a NVIDIA TitanX GPU with 12 GB memory. To avoid GPU memory overflow by the 3D model, the fed 3D volumes are automatically cropped to multiple sub-volumes when the size is larger than a certain threshold. The training was based on the Theano framework with CUDA 7.5 and cuDNN 5.0 support.

Figure 12:
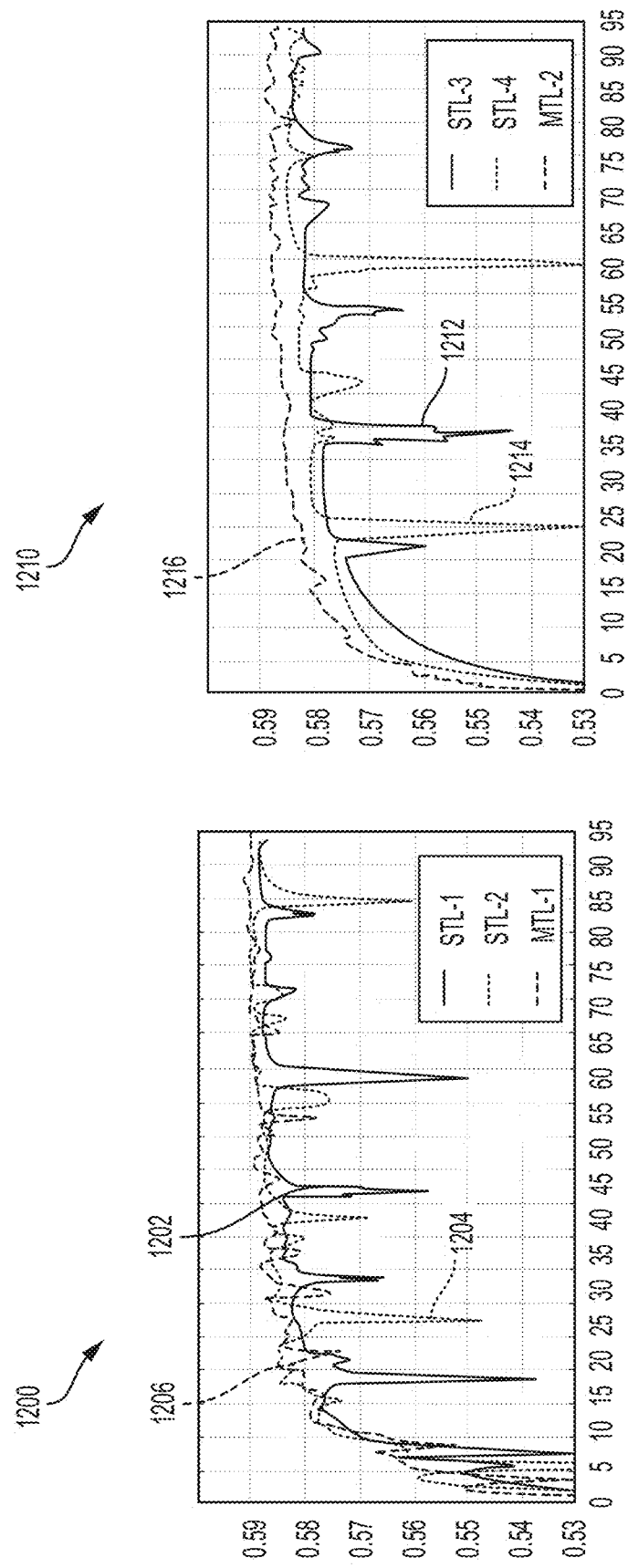
FIG. 12 illustrates a comparison of 3D DI2IN learning curves for testing data using different DI2IN experimental settings.

All the quantitative experiments were performed in 2 mm resolution. Table 2 shows the area under the curve (AUC) of the ROC curve of different DI2IN experiment settings, including learning rate $\lambda$, regularization weight $\omega$, and 2D/3D configuration. In Table 2, MTL-1 and MTL-2 represent results of bone segmentation in testing data using MTL-based 3D DI2IN with different DI2IN experiment settings. STL-1, STL-2, STL-3, and STL-4 represent results of bone segmentation using single task learning (STL)-based 3D DI2IN with different DI2IN experiment settings. 2D-t represents results of bone segmentation using a 2D DI2IN trained using transfer learning from VGG-net, and 2D-s represents results of bone segmentation using a 2D DI2IN trained from scratch. PBT represents results of bone segmentation using the existing PBT-based approach. FIG. 12 illustrates a comparison of 3D DI2IN learning curves for testing data using different DI2IN experimental settings. As shown in FIG. 12, image 1200 shows 3D DI2IN learning curves for STL-1 1202, STL-2 1204, and MTL-1 1206, which used a learning rate of $1e^{-3}$. Image 1210 shows 3D DI2IN learning curves for STL-3 1212, STL-4 1214, and MTL-2 1216, which used a learning rate of $1e^{-4}$. Overall, $\lambda=1e^{-3}$ shows slightly quicker convergence than $\lambda=1e^{-4}$, but with more frequent drop in the accuracy. The use of regularization with $\omega=0.01$ is able to reduce the frequency of accuracy dropping, but in the experiments with $\lambda=1e^{-4}$ it exhibits more severe drop amplitude. For each learning rate setting, MTL outperforms STL in both final accuracy and the learning curve stability. For 2D settings, transfer learning from VGG-Net (2D-t) is not superior to training from scratch (2D-s).

Figure 13:
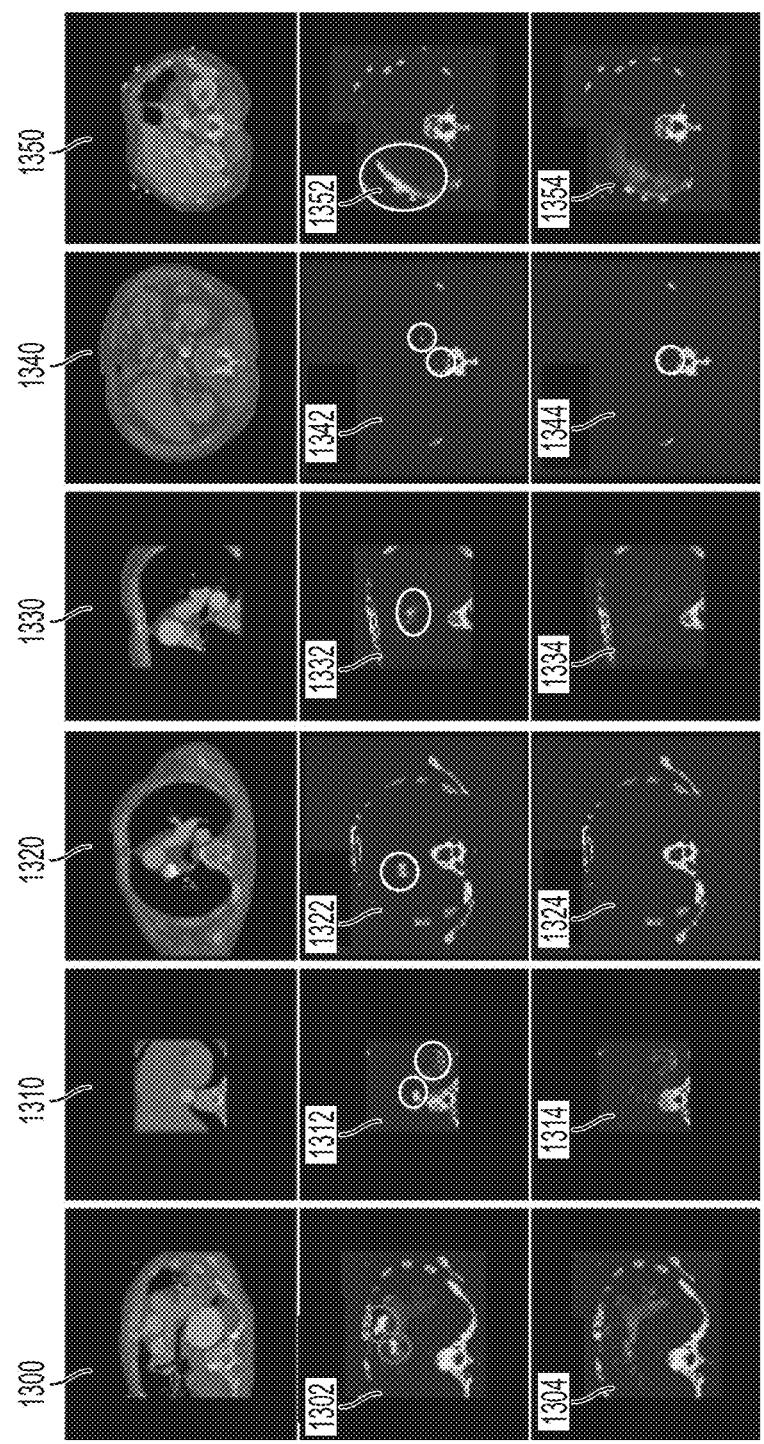
FIG. 13 illustrates a comparison of probability maps of axial CTA slices resulting from bone segmentation using an single task learning based DI2IN and an MTL-based DI2IN.

FIG. 13 illustrates a comparison of probability maps of axial CTA slices resulting from bone segmentation using an STL-based DI2IN and an MTL-based DI2IN. As shown in FIG. 13, images 1300, 1310, 1320, 1330, 1340, and 1350 show original axial CTA slices. Images 1302, 1312, 1322, 1332, 1342, and 1352 show probability maps resulting from bone segmentation using STL-1 in images 1300, 1310, 1320, 1330, 1340, and 1350, respectively. Images 1304, 1314, 1324, 1334, 1344, and 1354 show probability maps resulting from bone segmentation using MTL-1 in images 1300, 1310, 1320, 1330, 1340, and 1350, respectively. In the probability maps, whiter voxels correspond to higher probability of bones from the final Sigmoid output. Erroneous bone detection areas are circled in the probability maps 1302, 1312, 1322, 1332, 1342, and 1352 generated using STL-1. It is worth mentioning that the first column (images 1300, 1302, and 1304) is a very abnormal case with an aneurysm. Such an aneurysm does not exist in the training data set for STL. With MTL, the network is able to do a better job after seeing 24 times more training images.

Figure 14:
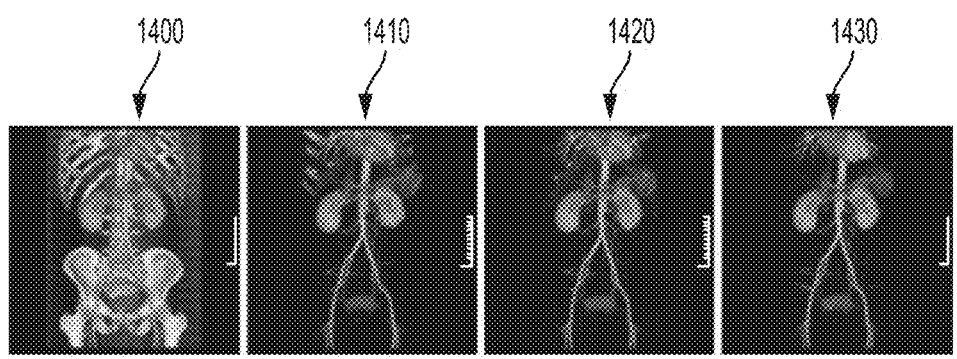
FIG. 14 illustrates exemplary results 3D visualizations of non-bone structures resulting from performing bone removal in a CTA volume.

Sometimes the quantitative number may not truly represent the end user experience. To evaluate the final outcome in the VRT view where the clinicians experience, the present inventors compared the proposed DI2IN framework with two existing approaches (watershed-SVM and PBT) on 329 unseen volumes. Two medical students subjectively evaluated the quality with severity scores in categories like "vessel cuts" and "bone fragments remaining". The score ranges from 0 to 3, where 0 means no issue at all and 3 means very obvious defect. Table 3 shows the histogram of the severity scores with body region details. It can be seen that watershed does a good job in keeping organs intact (e.g. kidneys), but the number of failure cases in bone remaining and vessel cut is large. PBT is slightly better in these two items, with worse performance in the other. Both STL and MTL DI2IN significantly outperform PBT and watershed. MTL is slightly better than STL, which is consistent with the quantitative findings. FIG. 14 illustrates exemplary results 3D visualizations of non-bone structures resulting from performing bone removal in a CTA volume. As shown in FIG. 14, image 1400 shows a 3D VRT visualization of the original CTA volume, image 1410 shows a 3D VRT visualization of the bone removal result using the PBT-based approach, image 1420 shows a 3D VRT visualization of the bone removal result using the SVM+watershed based approach, and image 1430 shows a 3D VRA visualization of the bone removal result using MTL DI2IN bone segmentation according to an embodiment of the present invention.

TABLE 2

|  | PBT | 2D-s | 2D-t | STL-1 | STL-2 | STL-3 | STL-4 | MTL-1 | MTL-2 |
| --- | --- | --- | --- | --- | --- | --- | --- | --- | --- |
| $\lambda$ | N/A | $1e^{-4}$ | $1e^{-4}$ | $1e^{-3}$ | $1e^{-3}$ | $1e^{-4}$ | $1e^{-4}$ | $1e^{-3}$ | $1e^{-4}$ |
| $\omega$ | N/A | 0.00 | 0.00 | 0.00 | 0.01 | 0.00 | 0.01 | 0.00 | 0.00 |
| AUC of ROC | 0.8423 | 0.9941 | 0.9936 | 0.9951 | 0.9959 | 0.9948 | 0.9950 | 0.9976 | 0.9958 |

TABLE 3

| Method | Issues | | | | | | | | | | | |
|---|---|---|---|---|---|---|---|---|---|---|---|---|
| | Missing Organs | | | | Remaining Bones | | | | Vessel Cut | | | |
| | 0 | 1 | 2 | 3 | 0 | 1 | 2 | 3 | 0 | 1 | 2 | 3 |
| Watershed[2] | 313 | 14 | 0 | 1 | 27 | 142 | 84 | 75 | 156 | 97 | 23 | 52 |
| PBT | 254 | 33 | 11 | 30 | 111 | 135 | 52 | 30 | 121 | 116 | 67 | 24 |
| STL-1 | 306 | 19 | 3 | 1 | 216 | 67 | 43 | 3 | 225 | 93 | 9 | 2 |
| MTL-1 | 319 | 6 | 3 | 1 | 203 | 107 | 18 | 1 | 229 | 97 | 3 | 0 |

| Region | Count |
|---|---|
| Neck | 135 |
| Thorax | 287 |
| Abdomen | 280 |
| Runoff | 92 |
| All | 329 |

Joint Bone Removal and Vessel Regression Using Pyramid Scene Parsing (PSP) Network In another embodiment of the present invention, bone removal is performed jointly with vessel regression. This embodiment addresses the vessel-cut problem caused by bone segmentation (bone removal) algorithms. In particular, one problem that may greatly influence bone-removal result is the appearance of a vessel-cut. Previous methods use post-processing techniques such as vessel tracing to fill those cuts. One possible drawback of using such post-processing methods is that the whole pipeline is not jointly optimized. This embodiment of the present invention provides a unified optimization framework to jointly regress vessels (trace vessels) and remove bone structures.

Figure 15:
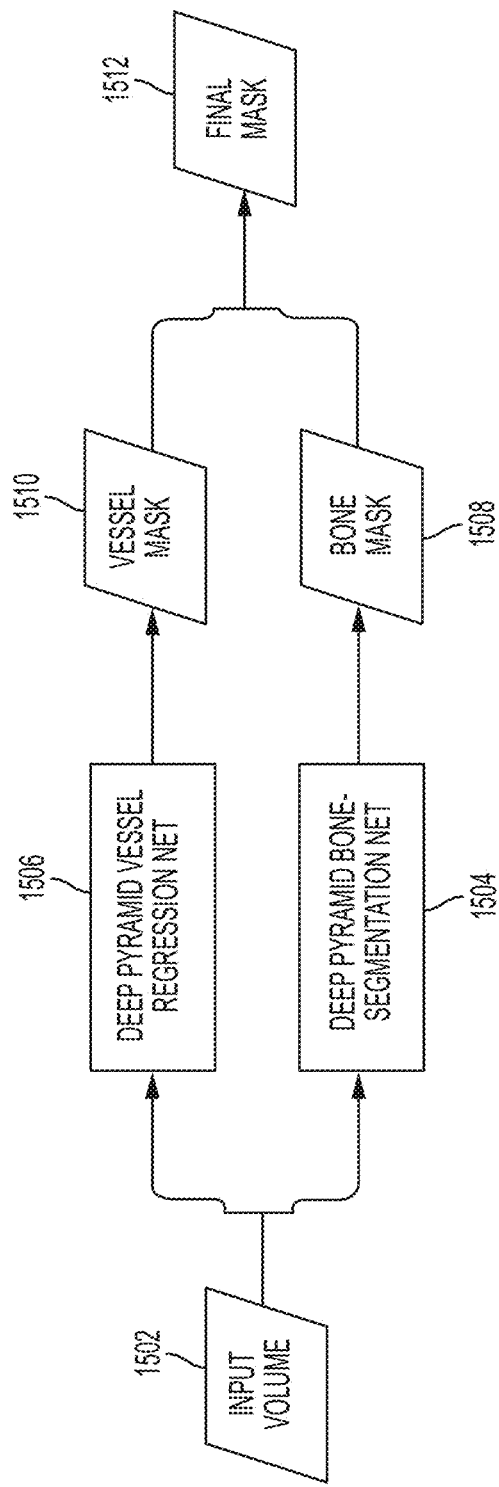
FIG. 15 illustrates a method for joint bone removal and vessel regression in a CTA volume according to an embodiment of the present invention.

FIG. 15 illustrates a method for joint bone removal and vessel regression in a CTA volume according to an embodiment of the present invention. As shown in FIG. 15, and input volume 1502 is received. In an exemplary embodiment the input image 1502 is a CTA volume. The input CTA volume 1502 may be received directly from an image acquisition device (i.e., a CT scanner) or may be received by loading a previously acquired CTA volume. In 3D volume rendering using VRT, only voxels with intensities higher than a certain intensity threshold (e.g., 132 HU) are displayed. Accordingly, masking/intensity thresholding can be applied to remove voxels with intensities less than the intensity threshold prior to performing the bone segmentation and vessel regression.

Figure 16:
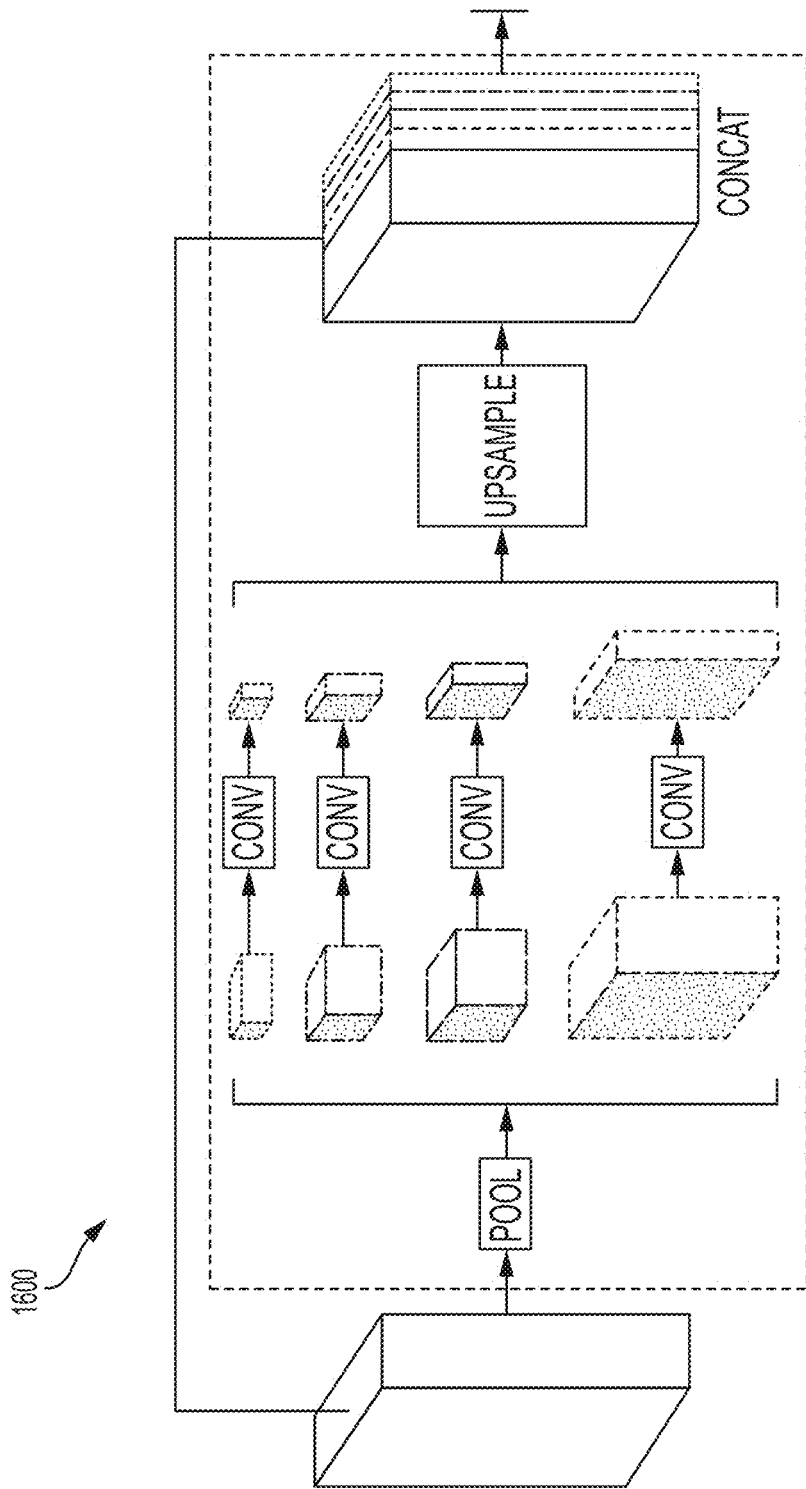
FIG. 16 illustrates an exemplary structure of a pyramid scene parsing (PSP) module.

Referring again to FIG. 15, a trained deep pyramid bone segmentation network 1504 performs bone segmentation in the input volume 1502 and a trained deep pyramid vessel regression network 1506 performs vessel regression (i.e., vessel tracing) in the input volume 1502. In an advantageous embodiment, respective DNNs are trained for bone segmentation and for vessel regression, the respective networks for both bone and vessel segmentation are each trained using a Deep Image-to-Image Network (DI2IN) with a structural adjustment—Pyramid Scene Parsing (PSP) on the decoder part of the DI2IN. Additional details regarding the DI2IN are described in U.S. Pat. No. 9,760,807, issued Sep. 12, 2017 and entitled "Deep Image-to-Image Network Learning for Medical Image Analysis," the disclosure of which is incorporated herein by reference in its entirety. FIG. 16 illustrates an exemplary structure of a PSP Module 1600. As shown in FIG. 16, the PSP module 1600 inputs a feature map, performs a pyramid of pooling operations to capture contexts of the input feature map in a coarse-fine-manner, convolves the pooled features, and then upsamples and concatenates the features. In an advantageous implementation, such a PSP module is added on the decoder part of the DI2IN architecture. In particular, a PSP module ca can be added at the last convolutional layer of the DI2IN architecture. Specifically, at the last convolutional layer of the DI2IN architecture, where the feature image size is the same as that the original image, a pyramid of the pooling operations is used to capture feature contexts in a coarse-to-fine manner. These features are convolved, upsampled to the original image size, and concatenated. Using such an ensemble of long- and short-range feature sets, the DI2IN-PSP network yields more accurate segmentation results for both bone segmentation and vessel segmentation.

Returning to FIG. 15, the trained deep pyramid bone segmentation network 1504 segments bone structures in the input volume 1502, resulting in a bone mask 1508, and the trained deep pyramid vessel regression network 1506 traces vessels in the input volume 1502, resulting in a vessel mask 1510. The bone mask 1508 and the vessel mask 1510 are the integrated to generate a final mask 1512 that is used to perform bone removal in the input volume 1502. In an exemplary implementation, a connected component analysis can performed based on the bone mask 1508 and the vessel mask 1510 to generate a final mask 1022 used for bone removal in the input image. A method for performing such a connected component analysis for generating the final mask is described in greater detail in United States Publication No. 2016/0328855, filed May 4, 2015 and entitled "Method and System for Whole Body Bone Removal and Vascular Visualization in Medical Image Data", the disclosure of which is incorporated herein in its entirety by reference.

The present inventors comparing the bone removal results on two datasets using the existing watershed+SVM based approach and joint bone removal and vessel regression using trained DI2IN-PSP networks. The experiments were performed on isotopically resampled datasets. The metrics are calculated by only considering voxels above a certain threshold (HU=123). Essentially, only bones, vessels, and some metal artifacts remained above the threshold. Therefore, the sensitivity and specificity approximately describes the correctness of bone and vessel segmentation, respectively. The methods were tested on 30 head and neck CTA volumes at 1 mm resolution. Table 4 illustrates the accuracy, sensitivity, and specificity of the bone removal results in the head and neck dataset using the previous technique ("Before") and using joint bone removal and vessel regression using trained DI2IN-PSP networks ("After"). The methods were also tested on 25 whole body CTA volumes at 2 mm resolution. Table 5 illustrates the accuracy, sensitivity, and specificity of the bone removal results in the whole body dataset using the previous technique ("Before") and using joint bone removal and vessel regression using trained DI2IN-PSP networks ("After").

TABLE 4

|  | Accuracy | Sensitivity | Specificity |
|---|---|---|---|
| Before | 0.957 | 0.984 | 0.834 |
| After | 0.978 | 0.988 | 0.921 |

TABLE 5

|  | Accuracy | Sensitivity | Specificity |
|---|---|---|---|
| Before | 0.948 | 0.950 | 0.974 |
| After | 0.992 | 0.994 | 0.979 |

Figure 17:
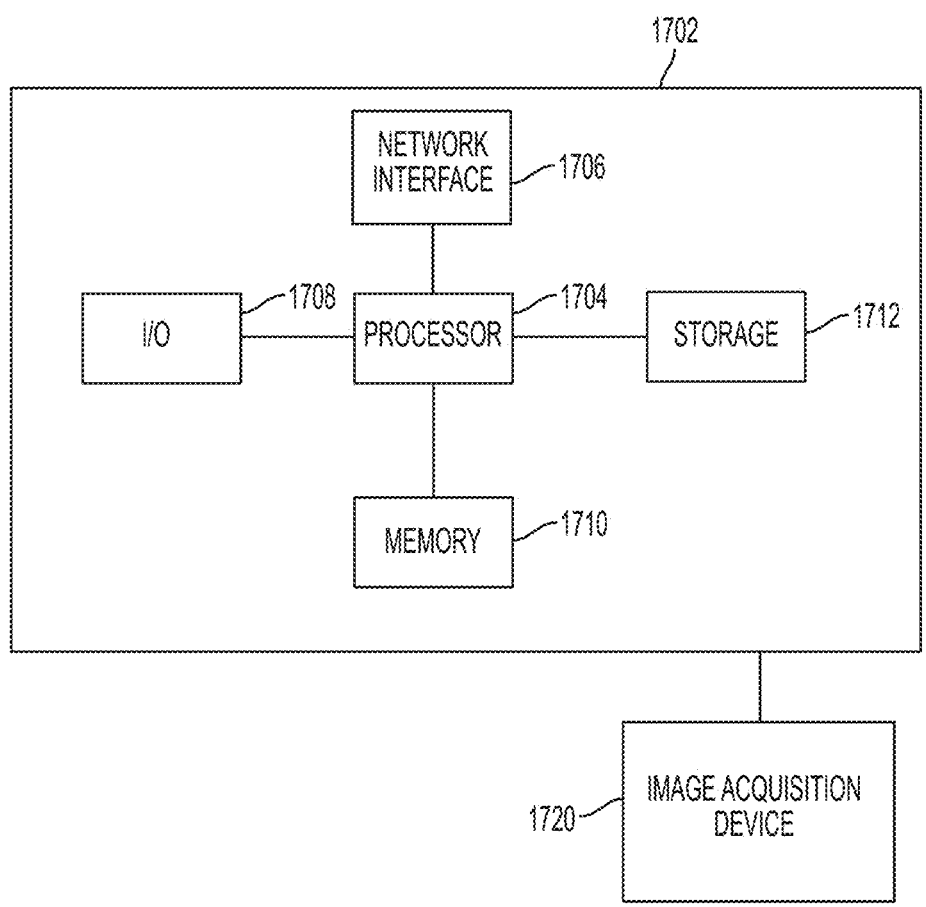
FIG. 17 is a high-level block diagram of a computer capable of implementing the present invention.

The above-described methods for deep learning based bone removal in medical images may be implemented on a computer using well-known computer processors, memory units, storage devices, computer software, and other components. A high-level block diagram of such a computer is illustrated in FIG. 17. Computer 1700 contains a processor 1704, which controls the overall operation of the computer 1700 by executing computer program instructions which define such operation. The computer program instructions may be stored in a storage device 1712 (e.g., magnetic disk) and loaded into memory 1710 when execution of the computer program instructions is desired. Thus, the steps of the methods of FIGS. 2, 10, and 15 may be defined by the computer program instructions stored in the memory 1710 and/or storage 1712 and controlled by the processor 1704 executing the computer program instructions. An image acquisition device 1720, such as an MR scanning device or a CT scanning device, can be connected to the computer 1700 to input image data to the computer 1702. It is possible to implement the image acquisition device 1720 and the computer 1700 as one device. It is also possible that the image acquisition device 1720 and the computer 1700 communicate wirelessly through a network. In a possible embodiment, the computer 1700 can be located remotely with respect to the image acquisition device 1720 and the method steps described herein can be performed as part of a server or cloud based service. In this case, the method steps may be performed on a single computer or distributed between multiple networked computers. The computer 1700 also includes one or more network interfaces 1706 for communicating with other devices via a network. The computer 1700 also includes other input/output devices 1708 that enable user interaction with the computer 1702 (e.g., display, keyboard, mouse, speakers, buttons, etc.). Such input/output devices 1708 may be used in conjunction with a set of computer programs as an annotation tool to annotate volumes received from the image acquisition device 1720. One skilled in the art will recognize that an implementation of an actual computer could contain other components as well, and that FIG. 17 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for automatic bone removal in a 3D medical image of a patient, comprising:
   segmenting bone structures in a 3D medical image of a patient by classifying voxels of the 3D medical image as bone or non-bone voxels using a deep neural network trained for bone segmentation, wherein segmenting bone structures in a 3D medical image of a patient by classifying voxels of the 3D medical image as bone or non-bone voxels using a deep neural network trained for bone segmentation comprises:
      segmenting the bone structures in the 3D medical image of the patient using a deep image-to-image network (DI2IN) trained using multi-task learning to segment the bone structures by generating a bone mask of the 3D medical image and to detect anatomical landmarks in the 3D medical image by generating a landmark heatmap of the 3D medical image; and
   generating a 3D visualization of non-bone structures in the 3D medical image by removing voxels classified as bone voxels from a 3D visualization of the 3D medical image.

2. The method of claim 1, wherein the 3D medical image of the patient is a computed tomography angiography (CTA) volume.

3. The method of claim 1, wherein generating a 3D visualization of non-bone structures in the 3D medical image by removing voxels classified as bone voxels from a 3D visualization of the 3D medical image comprises:
   setting an intensity value to zero for each the voxels classified as a bone voxels in the 3D visualization of the 3D medical image.

4. A method for automatic bone removal in a 3D medical image of a patient, comprising:
   segmenting bone structures in a 3D medical image of a patient by classifying voxels of the 3D medical image as bone or non-bone voxels using a deep neural network trained for bone segmentation, wherein segmenting bone structures in a 3D medical image of a patient by classifying voxels of the 3D medical image as bone or non-bone voxels using a deep neural network trained for bone segmentation comprises:
      jointly segmenting bone structures using a trained deep pyramid bone segmentation network and tracing vessel structures in the 3D medical image using a trained deep pyramid vessel regression network, wherein each of the trained deep pyramid bone segmentation network and the trained deep pyramid vessel regression network is a deep image-to-image network (DI2IN) with a pyramid scene parsing model added at a last convolutional layer of the DI2IN; and
      generating a final bone mask of the 3D medical image based on an initial bone mask generated by the trained deep pyramid bone segmentation network and a vessel mask generated by the trained deep pyramid vessel regression network; and generating a 3D visualization of non-bone structures in the 3D medical image by removing voxels classified as bone voxels from a 3D visualization of the 3D medical image.

5. The method of claim 4, wherein the 3D medical image of the patient is a computed tomography angiography (CTA) volume.

6. The method of claim 4, wherein generating a 3D visualization of non-bone structures in the 3D medical image by removing voxels classified as bone voxels from a 3D visualization of the 3D medical image comprises:

setting an intensity value to zero for each the voxels classified as a bone voxels in the 3D visualization of the 3D medical image.

7. An apparatus for automatic bone removal in a 3D medical image of a patient, comprising:

means for segmenting bone structures in a 3D medical image of a patient by classifying voxels of the 3D medical image as bone or non-bone voxels using a deep neural network trained for bone segmentation, wherein the means for segmenting bone structures in a 3D medical image of a patient by classifying voxels of the 3D medical image as bone or non-bone voxels using a deep neural network trained for bone segmentation comprises:

means for segmenting the bone structures in the 3D medical image of the patient using a deep image-to-image network (DI2IN) trained using multi-task learning to segment the bone structures by generating a bone mask of the 3D medical image and to detect anatomical landmarks in the 3D medical image by generating a landmark heatmap of the 3D medical image; and means for generating a 3D visualization of non-bone structures in the 3D medical image by removing voxels classified as bone voxels from a 3D visualization of the 3D medical image.

8. The apparatus of claim 7, wherein the 3D medical image of the patient is a computed tomography angiography (CTA) volume.

9. The apparatus of claim 7, wherein the means for generating a 3D visualization of non-bone structures in the 3D medical image by removing voxels classified as bone voxels from a 3D visualization of the 3D medical image comprises:

means for setting an intensity value to zero for each the voxels classified as a bone voxels in the 3D visualization of the 3D medical image.

10. An apparatus for automatic bone removal in a 3D medical image of a patient, comprising:

means for segmenting bone structures in a 3D medical image of a patient by classifying voxels of the 3D medical image as bone or non-bone voxels using a deep neural network trained for bone segmentation, wherein the means for segmenting bone structures in a 3D medical image of a patient by classifying voxels of the 3D medical image as bone or non-bone voxels using a deep neural network trained for bone segmentation comprises:

means for jointly segmenting bone structures using a trained deep pyramid bone segmentation network and tracing vessel structures in the 3D medical image using a trained deep pyramid vessel regression network, wherein each of the trained deep pyramid bone segmentation network and the trained deep pyramid vessel regression network is a deep image-to-image network (DI2IN) with a pyramid scene parsing model added at a last convolutional layer of the DI2IN; and means for generating a final bone mask of the 3D medical image based on an initial bone mask generated by the trained deep pyramid bone segmentation network and a vessel mask generated by the trained deep pyramid vessel regression network; and means for generating a 3D visualization of non-bone structures in the 3D medical image by removing voxels classified as bone voxels from a 3D visualization of the 3D medical image.

11. The apparatus of claim 10, wherein the 3D medical image of the patient is a computed tomography angiography (CTA) volume.

12. The apparatus of claim 10, wherein the means for generating a 3D visualization of non-bone structures in the 3D medical image by removing voxels classified as bone voxels from a 3D visualization of the 3D medical image comprises:

means for setting an intensity value to zero for each the voxels classified as a bone voxels in the 3D visualization of the 3D medical image.

13. A non-transitory computer readable medium storing computer program instructions for automatic bone removal in a 3D medical image of a patient, the computer program instructions when executed by a processor cause the process to perform operations comprising:

segmenting bone structures in a 3D medical image of a patient by classifying voxels of the 3D medical image as bone or non-bone voxels using a deep neural network trained for bone segmentation, wherein segmenting bone structures in a 3D medical image of a patient by classifying voxels of the 3D medical image as bone or non-bone voxels using a deep neural network trained for bone segmentation comprises:

segmenting the bone structures in the 3D medical image of the patient using a deep image-to-image network (DI2IN) trained using multi-task learning to segment the bone structures by generating a bone mask of the 3D medical image and to detect anatomical landmarks in the 3D medical image by generating a landmark heatmap of the 3D medical image; and generating a 3D visualization of non-bone structures in the 3D medical image by removing voxels classified as bone voxels from a 3D visualization of the 3D medical image.

14. The non-transitory computer readable medium of claim 13, wherein the 3D medical image of the patient is a computed tomography angiography (CTA) volume.

15. The non-transitory computer readable medium of claim 13, wherein generating a 3D visualization of non-bone structures in the 3D medical image by removing voxels classified as bone voxels from a 3D visualization of the 3D medical image comprises:

setting an intensity value to zero for each the voxels classified as a bone voxels in the 3D visualization of the 3D medical image.

16. A non-transitory computer readable medium storing computer program instructions for automatic bone removal in a 3D medical image of a patient, the computer program instructions when executed by a processor cause the process to perform operations comprising:

segmenting bone structures in a 3D medical image of a patient by classifying voxels of the 3D medical image as bone or non-bone voxels using a deep neural network trained for bone segmentation, wherein segmenting bone structures in a 3D medical image of a patient by classifying voxels of the 3D medical image as bone or non-bone voxels using a deep neural network trained for bone segmentation comprises:
jointly segmenting bone structures using a trained deep pyramid bone segmentation network and tracing vessel structures in the 3D medical image using a trained deep pyramid vessel regression network, wherein each of the trained deep pyramid bone segmentation network and the trained deep pyramid vessel regression network is a deep image-to-image network (DI2IN) with a pyramid scene parsing model added at a last convolutional layer of the DI2IN; and
generating a final bone mask of the 3D medical image based on an initial bone mask generated by the trained deep pyramid bone segmentation network and a vessel mask generated by the trained deep pyramid vessel regression network; and
generating a 3D visualization of non-bone structures in the 3D medical image by removing voxels classified as bone voxels from a 3D visualization of the 3D medical image.

17. The non-transitory computer readable medium of claim 16, wherein the 3D medical image of the patient is a computed tomography angiography (CTA) volume.

18. The non-transitory computer readable medium of claim 16, wherein generating a 3D visualization of non-bone structures in the 3D medical image by removing voxels classified as bone voxels from a 3D visualization of the 3D medical image comprises:
setting an intensity value to zero for each the voxels classified as a bone voxels in the 3D visualization of the 3D medical image.

* * * * *